(12) United States Patent
Esmaeli-Azad

(10) Patent No.: US 10,584,316 B2
(45) Date of Patent: *Mar. 10, 2020

(54) COMPOSTITION FOR REPROGRAMMING CELLS

(71) Applicant: Babak Esmaeli-Azad, San Diego, CA (US)

(72) Inventor: Babak Esmaeli-Azad, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/976,796

(22) Filed: May 10, 2018

(65) Prior Publication Data

US 2018/0258405 A1    Sep. 13, 2018

Related U.S. Application Data

(63) Continuation of application No. 15/636,548, filed on Jun. 28, 2017, now Pat. No. 9,988,607, which is a continuation of application No. 14/696,823, filed on Apr. 27, 2015, now Pat. No. 9,725,700, which is a continuation of application No. 12/637,738, filed on Dec. 14, 2009, now Pat. No. 9,045,737.

(60) Provisional application No. 61/122,360, filed on Dec. 13, 2008, provisional application No. 61/251,046, filed on Oct. 13, 2009.

(51) Int. Cl.
   *C12N 5/00*    (2006.01)
   *C12N 5/074*   (2010.01)
   *G01N 33/50*   (2006.01)

(52) U.S. Cl.
   CPC ........ *C12N 5/0696* (2013.01); *C12N 2501/02* (2013.01); *C12N 2501/065* (2013.01); *C12N 2501/415* (2013.01); *C12N 2503/00* (2013.01); *C12N 2506/1307* (2013.01); *C12N 2533/30* (2013.01); *C12N 2539/00* (2013.01); *G01N 33/5073* (2013.01); *G01N 2500/10* (2013.01)

(58) Field of Classification Search
   CPC .............. C12N 5/0696; C12N 2501/02; C12N 2501/065
   See application file for complete search history.

(56) References Cited

U.S. PATENT DOCUMENTS

| | | |
|---|---|---|
| 7,442,548 B2 | 10/2008 | Ludwig et al. |
| 8,530,238 B2 | 9/2013 | Yamanaka et al. |
| 8,703,413 B2 | 4/2014 | Daley et al. |
| 2003/0175902 A1 | 9/2003 | Sloma et al. |
| 2006/0030040 A1 | 2/2006 | Yang et al. |
| 2007/0042491 A1 | 2/2007 | Karp |
| 2008/0152630 A1* | 6/2008 | Ginis ............... A61K 35/28 424/93.7 |
| 2009/0304642 A1 | 12/2009 | Bakre |
| 2010/0267141 A1 | 10/2010 | Shi et al. |
| 2011/0088107 A1 | 4/2011 | Hanna et al. |
| 2012/0021519 A1 | 1/2012 | Ichida et al. |

OTHER PUBLICATIONS

Shu et al. Biomaterials 25:1339-1348, 2004 (Year: 2004).*
Takahashi and Yamanaka (Cell 126:663-676, 2006). (Year: 2006).*
Department of Health and Human Services, The Stem Cell. Stem Cells: Scientific Progress and Future Research Directions, Online article, Jun. 2001, pp. 1-4, Chapter 1.
Glycosan Biosystem, Extracel Hydrogel, online article, Aug. 23, 2011, p. 1 of 1,www.glycosan.com/ha_products/extracel_X.html.
Glycosan Biosystems Extracel-X References, online article, Aug. 23, 2011, p. 1 of 1. www.glycosan.com/ha_products/references.html.
Minronov et al. Biomaterials 26:7628-7635, 2005.
Nakagawa et al, Nat Biotechnol. (2008) 26:101-6.
Meissner et al Nat. Biotechnol. 25:1177-81.
Maheralli et al. (2007) Cell Stem Cell 1:55-70.
Stadtfeld et al. (2008) Cell Stem Cell.2:230-40.
Chen et. al. (2008) Cell 133: 1106-17.
Shi et al. (2008) Cell Stem Cell.2:525-528.
Teratocarcinomas and Embryonic Stem Cells: A Practical Approach (Robertson ed., Oxford: IRL Press, (1987).
Culture of Human Stem Cells (Freshney et al., eds., John Wiley & Sons, Hoboken, NJ) (Jun. 2007).
Sambrook et al. Molecular Cloning: A Laboratory Manual (2d ed., Cold Spring Harbor Laboratory Press, Cold Spring Harbor, N.Y. (1989)).
Current Protocols in Molecular Biology (eds. Ausubel, et al., Greene Publ. Assoc., Wiley-Interscience, NY).
Harlow and Lane, Antibodies, A Laboratory Manual, Cold Spring Harbor Laboratory, Cold Spring Harbor, N.Y. (1988).
Teratocarcinomas and Embryonic Stem Cells: A Practical Approach (1987) Oxford University Press.
Exp Hematol. (Nov. 14, 2009).
Li et al. (Nature (2009) 4601136-9.
Takahashi. et al ((2007), Cell 131:1-12).
Junying et al. ((2007) Science 318: 1917-1920).
Sato et al., Nat. Med. (2004) 10:55-63).
Bug et al. (2005) Cancer Res 65:2537-41).
Evans et al. (2007) J. of Biol. Chem. 282:33994-34028.
Chen & Tseng (2005) Mol. Pharmacol. 68:1203-13.

* cited by examiner

*Primary Examiner* — Marcia S Noble
(74) *Attorney, Agent, or Firm* — TJSL Patent Clinic

(57) ABSTRACT

Described here are three-dimensional microenvironment niches prepared from biomaterial compositions that support growth and self renewal of stem cells. The invention also provides methods for inducing pluripotency in a somatic cell using chemical compounds, as well as methods for screening for compounds that can induce pluripotency in a somatic cell.

10 Claims, 7 Drawing Sheets
Specification includes a Sequence Listing.

COMPOSITION FOR REPROGRAMMING CELLS

RELATED APPLICATIONS

This application is a continuation of U.S. patent application Ser. No. 15/636,548, filed Jun. 28, 2017, which is a continuation of U.S. patent application Ser. No. 14/696,823, filed Apr. 27, 2015, now U.S. Pat. No. 9,725,700, which is a continuation of U.S. patent application Ser. No. 12/637,738, filed Dec. 14, 2009, now U.S. Pat. No. 9,045,737, which claims the benefit of priority to U.S. Provisional Application Nos. 61/122,360, filed Dec. 13, 2008, and 61/251,046, filed Oct. 13, 2009, the entire disclosures of which are incorporated herein by reference.

BACKGROUND

Induction of pluripotent status in somatic cells by directed reprogramming in-vitro, (induced pluripotent stem (iPS) cells) offers great potential for the generation of disease- and patient-specific cell lines and cell therapy. Particularly, iPS cells provide the basis for practical generation of patient-specific cells for customized transplantation. Generation of iPS cells from mouse and human cells starting from somatic fibroblasts has recently been reported.

Two independent groups have identified laboratory protocols to induce iPS cell reprogramming. Takahasi et al. have reported that mouse and human skin cells can be transformed into ES-like cells by transduction of four genes: OCT3/4, SOX2, KLF4, and c-MYC (Cell. (2007) 131:861-72). Subsequent report demonstrated generation without c-MYC, making the procedure less prone to side effects such as induction of malignancy in host animal models (see Nakagawa et al., Nat Biotechnol. (2008) 26:101-6). A slightly different set of genes (OCT3, SOX2, NANOG and LIN28) has also been reported to reprogram human iPS cells. Such methods typically utilize selectable markers (e.g., neomycin resistance markers) to isolate iPS cells. However, alternative procedures that eliminate drug selection make such procedure more amenable to clinical applications in humans (Meissner et al. (2007) Nat. Biotechnol. 25: 1177-81.).

Although promising, iPS techniques have several shortcomings that limit application of this approach for use in the clinic, including: the potential of retroviruses to cause tumors in tissues derived from host iPS cells; low efficiency of induction (approximately 1 in 5000-10000 cells); the length of time the process requires (at least 20-24 days to generate and identify iPS cells); and the need to use drug resistance selection of iPS cells.

Thus, there remains an unmet need for patient-customized cell lines for cell therapy and tissue regeneration that are safe, can be rapidly prepared and identified in quantity without the use of antibiotics or other drug-based selection.

Ongoing basic and applied research in this field continues to elucidate important findings about the pluripotency status as well as means of induction of the "iPS" status. For instance, genome-wide analysis of two key histone modifications in iPS cells has indicated that iPS cells are highly similar to ES cells. In addition, it has been reported that transcription factor-induced reprogramming leads to the global reversion of the somatic epigenome into an ES-like state (Maheralli et al. (2007) Cell Stem Cell 1:55-70). iPS gene expression has been reported to be required for about 10 days, after which cells enter a self-sustaining pluripotent state suggesting that factor-induced reprogramming is a gradual process with defined intermediate cell populations that contain cells poised to become iPS cells (Stadtfeld et al. (2008) Cell Stem Cell. 2:230-40).

Two overlapping groups of pluripotency-associated transcription factors have been identified. The first group includes Nanog, Oct4, Sox2, Smad1 and Stat3. The second, smaller group includes c-Myc (an oncogene that boosts reprogramming efficiency), n-Myc, Zfx and E2f1. This may explain the characteristic cooperative function of pluripotency-promoting genes and the need to have a number of the key genes unregulated in iPS cells (Chen et. al. (2008) Cell 133: 1106-17). Finally, using a combined chemical and genetics approach for the generation of iPS cells, conditions that can potentially reduce the need for viral transduction of oncogenic transcription factors have been identified using neural progenitors and small molecules (Shi et al. (2008) Cell Stem Cell. 2:525-528.).

To date reprogrammed iPS cells have been generated from a variety of host cells including hematopoietic, hair follicular, dermal fibroblasts, neuronal cells, umbilical cord blood cells, adult ocular progenitor cells, and pancreatic islet progenitor cells. iPS cells have also been generated from host cells of a variety of animals including human, mouse, rat, monkey, cow, sheep, goat, pig, horse, dog, cat, rabbit, and chicken. Moreover, pluripotent stem cells such as iPS and hESC have been differentiated into a variety of cell types including heart muscle, liver, neuronal, hematopoietic, pancreatic, bone, skin, sperm and retinal pigment epithelial cells, and in at least one case, a complete animal has been generated with contributions from iPS cells.

Despite significant ongoing R&D efforts, the current unmet need for patient-customized cell lines that could be used for cell therapy and tissue regeneration is the main driver for development of alternative more practical iPS procedures, speeding the development of this early stage discovery phase procedure into the clinic.

DESCRIPTION OF THE INVENTION

Figure 1:
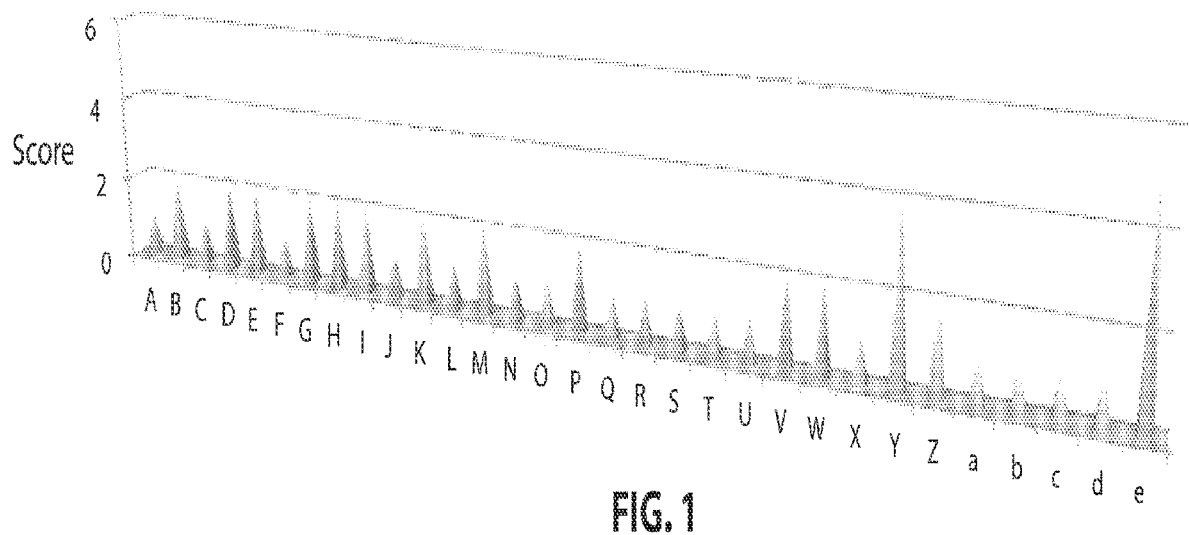
FIG. 1 is a plot of the scores of cell growth, survival and overall culture health on the various polymers listed in Table 1.

It is to be understood that both the foregoing general description and the following detailed description are exemplary and explanatory only and are not restrictive of the invention, as claimed. It must be noted that, as used herein and in the appended claims, the singular forms include plural referents; the use of "or" means "and/or" unless stated otherwise. Thus, for example, reference to "a cell" includes a plurality of such cells and reference to "the agent" includes reference to one or more agents and equivalents thereof known to those skilled in the art, and so forth. Moreover, it must be understood that the invention is not limited to the particular embodiments described, as such may, of course, vary. Further, the terminology used to describe particular embodiments is not intended to be limiting, since the scope of the present invention will be limited only by its claims.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless otherwise defined, all technical and scientific terms used herein have the same meaning as commonly understood by one of ordinary skill in the art to which this invention belongs. Suitable methods and materials are described below, however methods and materials similar or equivalent to those described herein can be used in the practice of the present invention. Thus, the materials, methods, and examples are illustrative only and not intended to be limiting. All publications, patent applications, patents, and other references mentioned herein are incorporated by reference in their entirety. In case of conflict, the present specification, including definitions, will control.

Standard techniques may be used for recombinant DNA, oligonucleotide synthesis, general cell and tissue culture, transfection (e.g., electroporation, lipofection, etc.), and the like. Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Teratocarcinomas and Embryonic Stem Cells: A Practical Approach (Robertson ed., Oxford: IRL Press, (1987)); Culture of Human Stem Cells (Freshney et al., eds., John Wiley & Sons, Hoboken, N.J.); Sambrook et al. Molecular Cloning: A Laboratory Manual (2d ed., Cold Spring Harbor Laboratory Press, Cold Spring Harbor, N.Y. (1989)); Current Protocols in Molecular Biology (eds. Ausubel, et al., Greene Publ. Assoc., Wiley-Interscience, NY); Harlow and Lane, Antibodies, A Laboratory Manual, Cold Spring Harbor Laboratory, Cold Spring Harbor, N.Y. (1988)) the entire contents of which are incorporated herein by reference for any purpose. Unless specific definitions are provided, the nomenclatures utilized in connection with, and the laboratory procedures and techniques of, cell biology, cell culture, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients Definitions As used herein, "biomaterial" refers to any natural or man-made material, that is composed of or is derived from, in whole or in part, living matter which performs, augments, or replaces a natural function, such as a polymer scaffolding perfused with cells or cell extracts.

"Cell-based therapy", as used herein, refers to treatment in which cells or derivatives or products thereof, are induced to supplement, replace, repair or treat diseased, damaged or destroyed cells or tissues.

"Cell culture" as used herein, refers to the growth of cells in vitro in an artificial medium for research or medical treatment.

As used herein "cell line" refers to cells of a particular type that can be maintained and grown in culture. Cell lines typically are homogeneous and well characterized, and can be stored (e.g. cryopreserved) for long periods of time. Certain cell lines may have a finite life span, while others may divide indefinitely.

"Cloning" refers to the generation of identical copies, e.g. of a region of a DNA molecule, or to generate and isolate genetically identical copies of a cell, or organism. In reference to cells grown in a tissue culture dish, a "clone" refers to a line of cells that is genetically identical to the original parent cell, that is produced by cell division (mitosis) of the original parent cell.

"Culture medium" as used herein, refers to a liquid that covers cells in a culture dish and contains nutrients to nourish and support the cells. Culture medium may include growth factors added to produce desired changes in the cells.

"Differentiation" as used herein, refers to process through which a stem cell loses its capacity for self-renewal and becomes a mature and definitive cell type, thereby acquiring the features of a specialized cell.

"Dedifferentiation" as used herein, refers to the process by which a differentiated cell reverts to a less specialized precursor, progenitor or stem cell state.

"Embryonic stem cells" or "ESCs" are primitive (undifferentiated) cells derived from the inner cell mass of an embryo (e.g. a human blastocyst) that are capable of dividing without differentiating for a prolonged period in culture, and, because they are pluripotent, can differentiate into any cell or tissue type. Mouse ESCs or mESCs can be injected into a mouse blastocyst and contribute to the formation of a mouse. Human ESCs or hESCs are not known to contribute to the formation of a human being.

"Embryonic stem cell line" refers to embryonic stem cells that have been cultured under in vitro conditions that allow proliferation without differentiation for months to years.

Human embryonic stem cell or hESC refers to a human pluripotent stem cell derived from the inner cell mass (ICM) of a human blastocyst.

"Epigenetic" refers to changes in phenotype and/or gene expression by mechanisms other than changes in the underlying DNA sequence.

"Gene" as used here, refers to a functional unit of heredity that is a segment or segments of nucleic acid found and directs synthesis of RNA, which typically leads to production of a protein. Genes include both RNA coding regions or sequences and control sequences, such as promoters located outside of RNA coding regions.

"High throughput screening" refers to technology for screening that employs automation and robotics to conduct hundreds or thousands of biological assay experiments within a short period of time. Typically, high throughput screening (HTS) systems will use rectangular plastic trays containing 96, 384, 1536, or 3456 wells (or more in microfluidic systems), where each well may hold a small amount of liquid sample containing cells. Automated liquid handling can add factors or compounds to test the effect on the cells. HTS can be used (for example) to screen hundreds of thousands of chemical compounds as potential drug candidates, or to identify factors that induce pluripotency or differentiation of a cell in culture.

Induced pluripotent stem cell" or "iPS cells" are a type of pluripotent stem cell, similar to an embryonic stem cell, formed by the induction of expression of certain embryonic genes in a somatic cell. The process of generating iPS cells, referred to as "reprogramming", can involve introduction of one or more, (often a combination of three to four) genes for e.g. transcription factors, delivered by retroviruses, into a somatic cell. iPS cells generated by viral, particularly retroviral (e.g. lentiviral) introductions of exogenous genes are referred to as "virally induced pluripotent stem cells" or "ViPS cells". iPS cells can also be induced by exposing somatic cells to soluble factors, including chemical compounds, biochemicals, polypeptides, carbohydrates, lipids and similar agents, and environmental niches that contain polymer matrices and immobilized or macromolecule-bound compounds and agents, without introduction of exogenous genetic material into the cells. Such iPS cells are referred to as "chemically induced pluripotent stem cells" or "CiPS cells". iPS cells also include cells that have been induced to pluripotency through a combination of the introduction of exogenous genes into a cell through viral or other vectors, and the treatment of cells with non-genetic compounds, agents, and environments.

"In vitro" as used herein refers to experiments, methods or processes that are performed or occur in an artificial environment, such as a laboratory culture tube or dish.

"In vivo" refers to experiments methods or processes that are performed or occur within the body of an organism, such as in animals in human clinical trials or treatments.

"Microenvironment" as used herein, refers to the molecules, including small molecules (such as compounds and other soluble factors), macromolecules (such as insoluble polymers), nutrients, growth factors, fluids, growth factors, cytokines and parameters such as pH, ionic strength and gas composition as well as adjacent cells, tissues, and the like, surrounding a cell in an organism or in the laboratory.

"Niche" refers to a microenvironment in which a cell is situated that is adapted to the phenotypic characteristics of the cell. Thus a "stem cell niche" is a microenvironment surrounding a stem cell that enables the stem cell to self-renew by dividing and giving rise to identical progeny cells. Changes in a stem cell niche may result in differentiation of the stem cell. Thus, there may be microenvironmental niches that promote differentiation of the stem cell into various cell lineages (i.e. ectoderm, mesoderm, and endoderm) as well as more specialized niches suitable for the further differentiation and specialization of cells into each of the types of cells in an organism (e.g. nerves, muscle, blood cells and the like).

"Multipotent" refers to the ability to develop into a limited number of cell types type of an organism. For example, hematopoietic stem cells are multipotent cells that can produce the various cell types found in blood.

By contrast, "pluripotent" cells are those that have the ability to give rise to all of the various cell types of the body, but cannot give rise to extra-embryonic tissues such as the amnion, chorion, and other components of the placenta, and cannot produce a living organism. Pluripotency can be demonstrated by providing evidence of stable developmental potential, to form derivatives of all three embryonic germ layers from the progeny of a single cell and to generate a teratoma after injection into an immunosuppressed mouse. Other indications of pluripotency include expression of genes known to be expressed in pluripotent cells, characteristic morphology and patterns of genomic DNA methylation known to be related to pluripotent epigenetic status.

"Totipotent" as used herein, refers to the ability of a cell, having the ability to develop into all types of cell including extraembryonic tissues (e.g. placenta) and to give rise to an entire organism (e.g. a mouse or human).

"Pluripotency factors" refers to the genes and/or gene products required to induce and/or maintain the pluripotent state of a stem cell. Certain methods for reprogramming involve introducing a combination of three to four pluripotency factor genes into a somatic cell using retroviruses. More recently, reprogramming methods have been derived that employ different, overlapping sets of pluripotency factors. Reprogramming methods described herein have been developed that use non-genetic agents, referred to generally as "chemicals" "compounds" or "compositions", that induce expression of endogenous pluripotency factors in a cell.

"Progenitor cell" is an early descendant of a stem cell that can differentiate, but cannot self-renew itself anymore. Pluripotent stem cells can differentiate into more specialized, non-pluripotent stem cells, such as hematopoietic stem cells. Thus, early progenitor cell descendents of a pluripotent stem cell may become committed to differentiate into hematopoietic lineages, including multipotent hematopoietic stem cells, and may therefore be referred to as hematopoietic progenitor cells.

"Proliferation" refers to the expansion in the number of cells by division (mitosis) of single cells into two daughter cells.

"Reprogramming" as used herein, refers to the process of changing or inducing a cell from a more differentiated state into a less differentiated state. Inducing a differentiated somatic cell (e.g. a dermal cell) to de-differentiate into a pluripotent stem cell (iPS), is accomplished through the process of reprogramming.

"Self-renewal" refers to the ability of a stem cell to divide and form more stem cells with identical properties to the parent stem cell, thereby allowing the population of stem cells to be replenished indefinitely.

"Somatic cell" as used herein, refers to differentiated body cells.

"Stem cells" are cells that have the ability to divide, giving rise to identical daughter cells (self-renewal) and progeny cells that can differentiate into specialized cells that are different from the stem cell parent. Stem cells can be totipotent, pluripotent or multipotent. Totipotent stem cells include zygotes. Pluripotent stem cells include ES cells derived from the inner cell mass of a blastocyst stage embryo, while multipotent stem cells include "adult stem cells" or "somatic stem cells" which are derived from the early embryos (post-blastocyst stage), fetus or adult.

"Undifferentiated" refers to a cell that has not yet developed into a specialized cell type.

"Expression" or "gene expression" as used herein refers to the conversion of the information from a gene into a gene product. A gene product can be the direct transcriptional product of a gene (e.g., mRNA, tRNA, rRNA, antisense RNA, ribozyme, structural RNA, or any other type of RNA) or a protein produced by translation.

"Operably linked" as used herein, means without limitation, that the coding region is in the correct location and orientation with respect to the promoter such that expression of the gene will be effected when the promoter is contacted with the appropriate polymerase and any required transcription factors.

The present invention is based on the concept that the environment of a cell, particularly the microenvironment immediately surround a cell influences its phenotype, and pluripotency or differentiation status. Thus, it was postulated that the more suitable an artificial microenvironment surrounding a cell could be for maintaining pluripotency, the more likely it would be that non-pluripotent cells in the same environment could be induced to a pluripotent state, and the more easily such somatic cells could be reprogrammed.

It was generally believed by the inventor that non-genetic compounds, such as small organic molecules, could be suitable for replacement of the introduction of exogenous pluripotency factors by gene transduction, through a reprogramming process that involved inducing iPS signal transduction pathways. The present invention provides methods for identifying non-genetic activators, such as small organic molecule activators, compounds, drugs, hormones, growth factors and the like, of iPS signal transduction pathways that can replace introduction of exogenous pluripotency factors by gene transduction for the induction of pluripotent status of somatic cells. The resulting cells are referred to as chemical iPS cells or CiPS.

In previous studies, the inventors developed and optimized an artificial in-vitro modeled biomaterial hydrogel microenvironment niche for hematopoietic stem cells (HSCs). The artificial microenvironment niche was found to support HSC proliferation and self-renewal, while maintaining the ability of HSCs to differentiated into hematopoietic non-stem cells. Moreover, it was discovered that the HSC microenvironment niche could be adapted to use as a self-renewal screening assay for hematopoietic stem cells (CD3$^{4+}$), through which potential activators of HSC self-renewal could be screened and identified. In developing the HSC microenvironment niche, human hematopoietic stem cells were cultured in a particular microenvironment and then contacted with potential self-renewal activation and maintenance factors, and self-renewal was measured as a means for optimizing the microenvironment niche. Activators thus identified could then be tested for their effects on somatic cells.

The present invention is based on the extension of studies with HSC environmental niche culture, to develop microenvironmental niches comprising biomaterial compositions optimized for pluripotent stem cells (i.e. that support growth and self renewal of pluripotent stem cells). It was reasoned that an optimized pluripotent stem cell microenvironmental niche could provide an appropriate environment in which to induce pluripotency of differentiated cells such as skin cells (i.e. dermal fibroblasts), thereby developing methods for inducing pluripotency and for identifying compounds that could induce pluripotency in a differentiated cell.

Among the teaching drawn upon to develop HSC microenvironmental niche culture, was the observation that certain hydrogels, particularly hyaluronan hydrogels, markedly improved the success of HSC growth and self-renewal, and facilitated screening efforts by permitting high-throughput screening in an array format.

Artificial In-Vitro Modeled Biomaterial Hydrogel Microenvironment Niche.

Hyaluronan hydrogels are remarkably versatile. They can be tailored to covalently attach peptides, non-covalently incorporate proteins (ECM proteins and cytokines), and to have different rigidities (compliances). Growth factors are retained within and slowly released from the hydrogel over the course of several weeks in culture. Growth factors are typically protected from proteolysis so that their bioactivity is maintained in longer term cultures. Incorporating growth factors (e.g. cytokines) in the hydrogel instead of the media allows for a dramatic reduction in the quantity needed. In certain embodiments, hyaluronan hydrogel chemistry available from Glycosan, (Salt Lake City, Utah) can be used. This is a xeno-free hydrogel containing thiol-modified hyaluronan and a polyethylene glycol diacrylate (PEGDA, MW 3400) cross linker that can gelatinize in less than 20 minutes for cell encapsulation.

Cells can be recovered from hyaluronan hydrogels using a variety of methods. For example, cells plated on the surface of the hydrogel can be recovered using traditional protocols for trypsin, collagenase, dispase and the like, including but not limited to, Accutase or TrypLE products. Hydrogel-encapsulated cells can be readily released using enzymatic digestion with hyaluronidase (an enzyme that digests the large HA polymer), thus dissolving the hydrogels, without harming the encapsulated cells.

In one embodiment of the invention, the microenvironment niche is a cell matrix array (CMA) adapted for rapid analytical identification and testing of the experimental parameters for optimum and derivation of CiPS cells. Such CMAs contain microspots of approximately 150 micron diameter containing factors contact printed (pin spotted) on a surface pre-coated with a formulation of hyaluronan hydrogel. This format facilitates multiplexing and permits direct analysis of cells by, e.g., ICC, staining for DAPI, alkaline phosphatase, and the like. Larger formats of the CMA are also contemplated for use in the methods of the present invention (e.g. 6-, 12-, 24-, 96- and 384-well plates, one well per hyaluronan and factor composition) and are suitable for applications that require larger yield of cells, such as for FACS (fluorescence activated cell sorting) analysis. In one aspect of the invention, CMA is performed using hyaluronan hydrogel containing a cocktail of ECM factors in mTeSR-1 media.

In developing the HSC microenvironment niche CMA assays for non-adherent hematopoietic stem cells, a method for preventing migration of the cells was required. Thus, 3-D cultures were used in which cells were embedded in the hyaluronan hydrogels. Although other cells, such as embryonic stem cells (ESCs), fibroblasts, and a vast array of differentiated cells can be grown on the surface of a culture dish, hydrogel or other matrix (2-D culture), it was fortuitously discovered that improvements in the morphological appearance of ESCs and higher plating efficiency could be obtained when cells were grown in 3-D culture versus 2-D culture. Thus, although methods have been previously reported to support the growth and self-renewal of ESCs in culture, for example, by growing HSCs in the presence of leukocyte inhibitory factor (LIF) and/or on layers of feeder cells (see e.g. Teratocarcinomas and Embryonic Stem Cells:

A Practical Approach (1987) Oxford University Press), and more recently that in the absence of animal cells or cell products (see e.g. U.S. Pat. No. 7,442,548; Ludwig et al., Nat. Methods. (2006) 3:637-46), the 3-D hydrogel microenvironment niche culture compositions and methods described herein provide superior conditions for screening for chemical induction of pluripotency. While not wishing to be bound by a particular theory, it is believed that a 3-D microenvironment which surrounds the cells with hydrogel polymer matrix and other biomaterials in connection with the hydrogel, more closely simulates the in vivo environment of a pluripotent stem cell than does a 2-D culture environment.

Thus, in one embodiment, the invention provides a 3-D microenvironment niche comprising a biomaterial composition that supports growth and self renewal of a stem cell, such as a pluripotent stem cell. In certain aspects of the invention, the stem cell is an embryonic stem cell such as a human embryonic stem cell (hESC). However, it should be noted that conditions provided by the three-dimensional microenvironment niche culture are generally suitable for growing a wide variety of cell types in which it is advantageous to surround the cell with hydrogel matrix-associated biomaterials. Cells contemplated for growth in the three-dimension microenvironment niche of the invention include pluripotent stem cells, adult stem cells (e.g., hematopoietic stem cells), and somatic cells. While the compositions of the microenvironment niche described herein have been optimized for growth of human ES cells through the elimination of e.g. animal cells, it will be well within the level of skill in the art to adapt the teachings of the present invention to culture of cells of other species, such as animals, particularly mammals, including but not limited to non-human primate, rodent, canine, feline, ovine, porcine and equine cells.

In certain embodiments of the invention, the 3-D microenvironment niche comprises a hyaluronan polymer. The optimized microenvironment niche containing this polymer was found superior to similar formulations containing Matrigel or more than a dozen other biopolymers. Thus, 3-D microenvironment niche cultures containing hyaluronan are preferred. However, it is well within the level of skill in the art to test new or additional polymers or polymer combinations for use in the 3-D microenvironment niche cultures of the invention based on the teachings presented below in EXAMPLE 1. There may be a reasonable expectation of success in substituting another biopolymer where the biopolymer has properties similar to hyaluronan, which is also known as a polymer of hyaluronic acid or hyaluronate, and is an anionic, non-sulfated glycosaminoglycan distributed widely throughout connective, epithelial, and neural tissues. Naturally occurring glycosaminoglycan polymers, particularly those found in extracellular matrices of human or non-human animal tissues are contemplated within the scope of the invention.

The optimized microenvironment niche according to the invention also contains at least one component selected from laminin, fibronectin, vitronectin; epidermal growth factor (EGF); fibroblast growth factor (FGF); Noggin; SIS; and EHS basement membrane. In certain embodiments, laminin is present at a concentration of 0.5 to 500 μm/ml, typically 1 to 100 μm/ml and most frequently about 5 μg/ml. In certain embodiments, fibronectin is present at a concentration of 0.5 to 500 μm/ml, typically 1 to 100 μm/ml and most frequently about 5 μg/ml. In certain embodiments, vitronectin is present at a concentration of 0.6 to 600 μg/ml, typically 1 to 100 μm/ml and most frequently about 6 μm/ml. In certain embodiments, EGF basement membrane is present at a concentration of 4 to 4000 ng/ml, typically 10 to 1000 ng/ml and most frequently about 40 ng/ml. In certain embodiments, FGF is present at a concentration of 20 to 220 ng/ml, typically 100 to 6000 ng/ml and most frequently about 220 ng/ml. In certain embodiments, Noggin is present at a concentration of 1.5 to 15000 μm/ml, typically 15 to 5000 μm/ml and most frequently about 150 ng/ml. In further embodiments, SIS is present at a concentration of 5 to 5000 μl/ml, typically 100 to 10000 ml and most frequently about 50 μg/ml. In yet further embodiments, EHS basement membrane is present at a concentration of 5 to 5000 μm/ml, typically 100 to 1000 μm/ml and most frequently about 50 μm/ml.

In one aspect of the invention, the microenvironment niche according to the invention comprises about 5 μg/ml fibronectin, about 6 μm/ml vitronectin, about 40 ng/ml EGF, about 220 ng/ml FGF, about 150 ng/ml Noggin, about 50 μl/ml SIS and 50 μm/ml EHS basement membrane. In certain embodiments of the invention, one or more or all of the aforementioned components is included in hydrogel formulation itself; in other embodiments, one or more or all of the aforementioned components is included in included in a soluble culture medium in which the hydrogel is bathed; in yet further embodiments, one or more or all of the aforementioned components is included in both the hydrogel formulation and is present in a soluble culture medium in which the hydrogel is bathed.

Suitable adaptations and variations of the microenvironment niche can be made by the skilled artisan by following the teaching outlined in EXAMPLES 1 and 2. Particularly, providing a basic microenvironment niche biomaterial composition described herein, adding or substitution one or more additional biomaterials, nutrients, growth factors, polymers or the like, and comparing the growth and self renewal of stem cells, such a pluripotent stem cells, e.g. hESCs in the presence of the basic microenvironment niche biomaterial composition and in the modified microenvironment niche composition, scoring cell growth, survival and appropriate stem cell morphology, and selecting additions or substitutions that improve the score of cells grown in the modified 3D microenvironment niche composition.

CMA-Based Screening for Induction of Pluripotency

The present invention also provides CMA-based drug screening using the 3-D microenvironment niche biomaterial compositions described herein. In certain aspects of the invention the CMA is be adapted to high throughput screening. Compound screening can be performed within this optimal 3-D microenvironment niche biomaterial compositions assay background to accurately identify, select and quantify self renewal of stem cells or pluripotency induction of somatic cells.

In one embodiment, the present invention provides a method of screening for compounds that induce pluripotency of a somatic cell, that includes the steps of contacting a test compound with a somatic cell that is in contact with (i.e. surrounded by or embedded within) a three 3-D microenvironment niche described herein; measuring expression of an endogenous pluripotency factor in the somatic cell; and selecting test compounds that increase the expression of the endogenous pluripotency factor in the somatic cell. As described in greater detail below in the EXAMPLES, an increase in the expression of certain endogenous pluripotency factors in the somatic cell correlates to induction of pluripotency. Endogenous pluripotency factors contemplated for use in screening methods of the invention can be any endogenous gene, the expression of which is correlated to a phenotype or property of a pluripotent stem cell, such as an undifferentiated phenotype, cell growth and self-renewal, and an ability to differentiate into all three germ layers. Such pluripotency factors include, but are not limited to, OCT3/4, SOX2, LIN28, KLF4, cMYC and NANOG. In addition, it may be of benefit to measure expression of an endogenous factors in the somatic cell that support or promote pathways known to be activated in pluripotent cells, such as the Wnt pathway. In yet further embodiments, expression of additional pluripotency factors or repression of pluripotency-suppressive factors may be targeted and measured for specific types of somatic cells. For example Takenaka et al. have reported ViPS generation from cord blood cells using OCT3/4, SOX2, Krüppel-like factor 4, c-MYC expressing lentiviruses in combination with p53 knockdown (see Exp Hematol. (2009) Nov. 14); and Li et al. (Nature (2009) 4601136-9) have reported increased efficiency of ViPS by including inhibition of Ink4/Arf in mouse and human cells.

In certain embodiments of the invention, compounds are preselected for screening based on known or reported effects on abilities to affect expression of pluripotency factors or pathways thought to be important in regulating expression of one or more pluripotency factors or promoting a phenotype or characteristic of a pluripotent stem cell, such as growth, characteristic morphology, self-renewal, and ability to differentiate. Thus, for example, chemical inducers of iPS cells can also be pre-selected or screened based on their ability to trigger the ViPS process, which has been shown to require exogenous expression of 3 main iPS factors: Oct3/4, Sox-2, and Klf4. Thus, one embodiment the present invention provides methods for identifying CiPS activators by culturing cells in a biomaterial hydrogel microenvironment niche, contacting the cultured cells with potential activators, and measuring the effect of potential activators on the expression of Oct3/4, Sox-2, and/or Klf4. Expression can be measured by any suitable means known in the art. In one embodiment, expression is measured using constructs in which promoter regions of Oct3/4, Sox-2, and/or Klf4 are cloned upstream of a green fluorescent protein or other reporter gene. In certain embodiments, the time course and kinetics of promoter-reporter gene expression is compared to that which occurs during ViPS induction as described in Takahashi. et al ((2007), Cell 131:1-12); Junying et al. ((2007) Science 318: 1917-1920); Meissner et al. ((2007) Nature Biotechnology 25 (10): 1177-1181)); and Nakagawa et al. ((2007) Nature Biotechnology doi:10.1038/nbt1374)).

Using a pre-selection approach, a cocktail of four compounds was discovered that could replace the expression of pluripotency factors OCT3/4, SOX2, NANAOG, and KLF4 from exogenous polynucleotides virally introduced into human dermal fibroblasts, (see EXAMPLE 3, below). Further compounds were discovered upon screening a preselected library of compounds, that could improve or enhance the efficiency of induction of pluripotency, as illustrated below (see e.g. FIGS. 7 and 8, and accompanying text).

Of particular interest for pre-selection are: compounds that activate Wnt pathway; compounds that activate the cyclooxygenase pathway and its cross talk with the Wnt pathway; compounds with histone deacetylase activity; compounds that increase OCT3/4 expression; compounds that increase Sox-2 expression; compounds that increase Klf4 expression; compounds that increase Nanog expression; and compounds that inhibit p53 and related pathways.

Using methods of the invention, compound classes that influence signal transduction pathways and play key roles in self renewal signal transduction pathways were identified in a preselected library compounds. From approximately 1800 compounds, 7 compounds have been identified that together or in various combinations, can induce pluripotency of HDF cells using a CMA-based drug screening of the invention with the 3-D microenvironment niche biomaterial compositions described herein. Of particular interest are compounds that stimulate multiple pluripotency factors. For example, compound valproic acid was found to stimulate expression of both SOX2 and OCT4 promoters (see FIG. 7). It may thus be possible to chemically induce pluripotency of somatic cells using only one or a limited number of chemical inducers.

In one aspect of the invention, libraries containing uncharacterized compounds, such as combinatorial libraries of compounds, can be screened for their ability to effect self-renewal by stimulating expression of endogenous pluripotency factors. The screening methods of the invention can also be used in conjunction with structure assisted design, medicinal chemistry, and structure activity relationship analysis of small molecule activator/inhibitors of self-renewal pathways, providing alternatives for compound structure availability.

Cells suitable for use in iPS trigger assays can be any cells, and are preferably mammalian somatic cells, such as mouse or human somatic cells. In certain embodiments, the cells are fibroblasts, (e.g., human dermal fibroblasts (HDF)).

In certain embodiments of the invention CiPS cells are characterized at the cellular and molecular level and compared to V iPS cells. In these aspects, cells are grown and induced for CiPS in the 3-D microenvironment niche biomaterial compositions of the invention. Control cells are induced using genetic (e.g., viral) transduction of iPS cells based on established protocols that are known in the art. Samplings of cells at time=0, 2, 4, 6, 8, 10, 12, 14, 16, 18, 20, 22, 24 days post treatment, scored for characteristic ES cell morphology, and validation of cell reprogramming. Cell reprogramming can be measured by any methods known in the art, including but not limited to, expression of pluripotency associated genes using, for example, RT-PCR; immunoassay for pluripotency biomarker expression; methylation analysis of promoters affected by stem cell specific epigenetic events, such as the Oct4 and Nanog promoter; and the ability to form teratomas in SCID mice, giving rise to all three embryonic germ layers.

In certain embodiments, cultures maintained for 24 days are analyzed for the presence of iPS colonies by morphological identification. CiPS and ViPS colonies (subclones) are then isolated, propagated and analyzed. In addition, the similarities and/or differences between chemically and genetically induced iPS cells can be identified at the molecular and cellular level, and the rate and efficiency of iPS colony induction can be compared. Other standard culture analyses such as routine cell viability testing using dye exclusion, are performed throughout the methods of the invention.

CMA methods of the invention permit rapid testing of a variety of parameters, including various chemical activators, in a combinatorial manner making possible comprehensive analysis of agonistic versus antagonistic, and "cross talk" effects (e.g. a growth factor cross talk with an ECM factor or a rigidity feature).

Chemical Induction of Pluripotency in Somatic Cells

Using the overall scheme described above, an exemplary protocol for chemical induction was devised that resulted in CiPS induction efficiencies equal to or greater than those observed with ViPS in parallel. Thus, the present invention also provides a method for inducing pluripotency of a somatic cell, that includes the steps of providing a somatic cell in contact with a 3-D microenvironment niche biomaterial composition that supports growth and self-renewal of a stem cell (e.g. an embryonic stem cell, such as a hESC), and contacting the somatic cell with at least one compound that induces expression of at least one endogenous pluripotency factor. The somatic cell can be any non-pluripotent cell, such as a somatic stem cell (e.g. Adult stem cells, HSCs) and somatic non-stem cells, such as a fibroblasts (e.g. a dermal fibroblast), and can be from a cultured cell such as a cell line or primary culture, or it can be a cell that has not previously been cultured, such as from a tissue or organ (e.g. a biopsy specimen) or cell from a bodily fluid, such as blood, urine, amniotic fluid or lymph. Contemplated for use in the present invention are cells from a variety of organisms, particularly mammals, including but not limited to human and non-human primates (e.g. monkey, chimpanzees, macaques, baboons and the like) rodents (e.g. mice, rats, hamsters), canines, felines, ovines, porcines and equines.

In one embodiment of the invention, the cell is embedded in the 3-D microenvironment niche by preparing a hydrogel matrix containing a biomaterial composition of the invention, and mixing the hydrogel with the cell; and allowing the hydrogel to solidify. In this manner, the cell is completely surrounded by the microenvironment niche.

In certain aspects of the invention, the microenvironment niche includes a hyaluronan hydrogel polymer and about 5 µg/ml fibronectin, about 6 µg/ml vitronectin, about 40 ng/ml EGF, about 220 ng/ml FGF, about 150 ng/ml Noggin, about 50 µl/ml SIS and 50 µg/ml EHS basement membrane.

After plating, the cell may optionally be treated with Colcemid or another cell synchronization agent, which has been found to improve CiPS induction efficiency. The cell is then cultured in microenvironment niche biomaterial composition for 1-14 days, typically 3-10 days and most often for 7 days in the with additions and changes of fluid media as needed (approximately every 2 days).

iPS cell induction is accomplished by contacting the cell with at least one compound that induces expression of at least one endogenous pluripotency factor, as described above. The at least one pluripotency factor can be OCT3/4, SOX2, LIN28, KLF4, cMYC or NANOG. In certain aspects of the invention, the at least one pluripotency factor activates a Wnt pathway, activates a Cyclooxygenase pathway, or inhibits a p53 activity. An exemplary combination of compounds includes at least one of 6-bromoindirubin-3'-oxime (BIO); valproic acid; prostaglandin J2; and prostaglandin E2 and optionally); indirubin-5-nitro-3'-oxime (INO); 1-(4-Methylphenyl)-2-(4,5,6,7-tetrahydro-2-imino-3(2H)-benzothiazolyl)ethanone HBr (Pifithrin-α); and/or 2-(3-(6-Methylpyridin-2-yl)-1H-pyrazol-4-yl)-1,5-naphthyridine.

In certain embodiments, induction is accomplished by contacting the cell with a combination of 6-bromoindirubin-3'-oxime (BIO); indirubin-5-nitro-3'-oxime (INO); valproic acid; 2-(3-(6-Methylpyridin-2-yl)-1H-pyrazol-4-yl)-1,5-naphthyridine; 1-(4-Methylphenyl)-2-(4,5,6,7-tetrahydro-2-imino-3(2H)-benzothiazolyl)ethanone HBr (Pifithrin-α); prostaglandin J2; and prostaglandin E2. For example, the final composition of chemical inducers can include 0.1 to 100 µM, frequently 0.4 to 40 µM, and typically about 4 µM 6-bromoindirubin-3'-oxime (BIO); 0.1 to 100 µM, frequently 0.4 to 40 µM, and typically about 4 µM indirubin-5-nitro-3'-oxime (INO); 0.05 to 50 mM, frequently 0.2 to 20 mM, and typically about 2 mM valproic acid; 0.1 to 1000 nM, frequently 2.5 to 250 nM and typically about 25 mM 2-(3-(6-Methylpyridin-2-yl)-1H-pyrazol-4-yl)-1,5-naphthyridine; 0.1 to 1000 µM, frequently 3 to 300 µM, and typically about 30 µM 1-(4-Methylphenyl)-2-(4,5,6,7-tetrahydro-2-imino-3(2H)-benzothiazolyl)ethanone HBr (Pifithrin-α); 0.5 to 500 µM, frequently 1 to 100 µM and typically about 10 µM prostaglandin J2; and 0.5 to 500 µM, frequently 1 to 100 µM and typically about 10 µM prostaglandin E2.

In one embodiment, the induction is accomplished by the addition chemical inducers to a final concentration of about 4 µM 6-bromoindirubin-3'-oxime (BIO); about 2 mM valproic acid; about 10 µM prostaglandin J2; about 10 µM prostaglandin E2; and optionally about 4 µM indirubin-5-nitro-3'-oxime (INO); about 25 mM 2-(3-(6-Methylpyridin-2-yl)-1H-pyrazol-4-yl)-1,5-naphthyridine; and/or about 30 µM Pifithrin-α.

The induction is allowed to proceed for about 1-6 weeks, frequently 2-3 weeks and most typically about 32 days with changes of the soluble medium and replenishment of chemical inducers as needed to maintain the viability of the cells (50% media change approximately every 2 days).

Following induction, cells are dissociated from the 3-D microenvironment niche matrix and iPS cells generated thereby can be plated in either 3-D or 2-D culture, (such as by plating on top rather than within the microenvironment niche biomaterial composition of the invention), and without the presence of inducers. Notably, the CiPS methods of the invention produce iPS cells with phenotypic characteristics of ViPS cells and similar to hES cells (see EXAMPLE 8 below), without the transfer of exogenous pluripotency factors to the cells, without the use of viral vectors and without continued, long-term presence of the inducing agent.

Chemically Induced iPS Cells (CiPS Cells)

In yet another embodiment, the present invention provides CiPS cells induced by a method of the invention. For example, the invention includes pluripotent stem cells induced by at least one or a combination of 6-bromoindirubin-3'-oxime (BIO); valproic acid; prostaglandin J2; prostaglandin E2; and optionally indirubin-5-nitro-3'-oxime (INO); 2-(3-(6-Methylpyridin-2-yl)-1H-pyrazol-4-yl)-1,5-naphthyridine; and/or Pifithrin-α.

Chemically induced pluripotent cells of the invention have at least one characteristic of an ES cell or a reprogrammed, ViPS cell, such as characteristic morphology in culture, self-renewal, stable developmental potential to form derivatives of all three embryonic germ layers from the progeny of a single cell, ability to generate a teratoma after injection into SCID mouse giving rise to all three embryonic germ layers; patterns of genomic DNA methylation known to be related to pluripotent epigenetic status; expression of pluripotency associated genes and presence of biomarkers of pluripotency.

EXAMPLES

Example 1: Pluripotent 3D Culture
Microenvironment Screening and Development

Materials.

Xeno Free thiol-modified hyaluronan (HA) containing thiol-modified collagen (TMC) (collectively HAF) and polyethylene glycol diacrylate (CL) were purchased from Glycosan BioSystems, Inc. (Salt Lake City, Utah). Human dermal fibroblasts (HDF) were purchased from Invitrogen corporation (Carlsbad, Calif.). mTeSR®1 medium and 10× collagenase/hyaluronidase were purchased from Stem Cell Technologies, Inc. (Vancouver, BC, Canada). Laminin, fibronectin and vitronectin, and soluble form of basement membrane purified from Engelbreth-Holm-Swann (EHS) tumor containing laminin I, collagen IV, entactin, heparin sulfate proteoglycan were from Trevigen Corp. (VWR Scientific, West Chester, Pa.). Epidermal Growth Factor and Fibroblast Growth Factor were from Collaborative Research, Inc. (Bedford, Mass.). 6-bromoindirubin-3'-oxime (BIO) and 2-(3-(6-Methylpyridin-2-yl)-1H-pyrazol-4-yl)-1, 5-naphthyridine were purchased from EMD4 Biosciences Corp (Poland). Indirubin-5-nitro-3'-oxime (INO) (custom synthesis). Prostaglandins J2 and E2 were from Cayman Chemicals Corp. (Ann Arbor, Mich.). Valproic Acid (2 mM), colcemid (N-deacetyl-N-Methylcolchicine) were from Sigma-Aldrich (St. Louis Mo.). 1-(4-Methylphenyl)-2-(4,5,6,7-tetrahydro-2-imino-3(2H)-benzothiazolyl)ethanone. HBr (Pifithrin-α) was from Enzo Life Sciences (San Diego, Calif.).

Cells and Media.

Human embryonic stem cells (hESC, MEL-1; Millipore Corp.; Billerica, Mass.) and human dermal fibroblasts (HDF; Invitrogen; Carlsbad, Calif.) cells were used for screening of conditions. In all cases, after preparation, biomaterial microarrays were seeded with 100,000 cells in a 100 mm culture dish using fully supplemented mTeSR-1 medium (Stem Cell Technologies; Vancouver, BC, Canada). Cells were also grown on Matrigel (BD Biosciences) coated plates in presence of mTeSR-1 medium as a control.

Pig Small Intestine Submucosa (SIS) Extract.

Small intestinal submucosa (SIS) was prepared from porcine intestine obtained from a local meat processing plant. Intestine was rinsed free of contents, everted and the superficial layers of the mucosa were removed by mechanical delamination. The tissue was reverted to its original orientation and the external muscle layer removed. The prepared SIS tube was split open longitudinally and rinsed extensively in water to lyse any cells associated with the matrix and to eliminate cell degradation products. Immediately after rinsing, SIS was frozen in liquid nitrogen and stored at −80° C. Frozen tissue was sliced into 1 cm cubes, pulverized under liquid nitrogen with an industrial blender to particles less than 2 mm$^2$ and stored at −80° C. prior to use. SIS powder was suspended in extraction buffer (4 M guanidine, 2 M urea, 2 M MgCl$_2$ and 2 M NaCl, in 50 mM Tris-HCl, pH 7.4) (25% w/v) containing phenylmethyl sulphonyl fluoride, N-ethylmaleimide, and benzamidine (protease inhibitors; 1 mM each) and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000×g to remove any insoluble material and the supernatant was used immediately or lyophilized for long term storage.

Fresh Liver Crude Extract.

Freshly isolated liver from porcine was obtained from a local meat processing plant. Immediately after isolation the liver was frozen in liquid nitrogen and stored at −80° C. Frozen tissue was sliced into 1 cm cubes, pulverized under liquid nitrogen with an industrial blender to particles less than 2 mm$^2$ and stored at −80° C. prior to use. Using extraction buffer made of 4 M guanidine, 2 M urea, 2 M MgCl$_2$ and 2 M NaCl each prepared in 50 mM Tris-HCl, pH 7.4. Liver powder was suspended in extraction buffers (25% w/v) containing phenylmethyl sulphonyl fluoride, N-ethylmaleimide, and benzamidine (protease inhibitors) each at 1 mM and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000×g to remove any insoluble material and the supernatant was used immediately or lyophilized for long term storage.

Biomaterial Microarray Slide Preparation.

Epoxy coated glass slides (Corning) were dip coated into 4% (w/v) poly hydroxyethyl methacrylate (pHEMA; Aldrich; Milwaukee, Wis.) solution in ethanol and dried for 3 days prior to use. Polymers were purchased from Aldrich, Polysciences (Warrington, Pa.), and Birmingham Polymers (Birmingham, Ala.). Polymers were dissolved to 10% w/v in dimethylformamide (DMF), and then mixed in 384 well plates. Monomers were printed onto the slides using CMP6 or CMP3 pins (Telechem International, Sunnyvale, Calif.) with a Pixsys 5500 robot (Cartesian Technologies, Inc.: Ann Arbor, Mich.). To increase the thickness of polymer spots, six layers of polymer were printed onto each spot. The polymer arrays were then dried at <50 mTorr for at least 7 days. Polymer arrays were sterilized by exposure to UV for 30 min on each side, and then washed twice with PBS for 30 min and then twice with medium for 30 min prior to use.

Combinatorial mixtures (see below) of a) Polymers, b) ECM factors, c) Growth Factors, and d) Crude factors were screened in both cell embedded (3D) and non-embedded (2D) format.

Analysis and Scoring.

After 5 days in culture, each spot was visually examined and scored for cell growth, survival and overall appearance of culture health, and compared to controls grown on Matrigel using the following relative scoring system:

| Numerical Score | Assessment of Culture Growth, Survival and Culture Health |
| --- | --- |
| 10 | Much better than Matrigel control |
| 5 | Similar to Matrigel control |
| 1 | Much worse than Matrigel control |

Healthy hESC had the characteristic, undifferentiated appearance of compact cells having clearly defined cell borders. Healthy cultures of both hESC and HDF showed evidence of active mitosis. Scores from both cell type (hESC & HDF) were averaged for each condition.

Polymer Screening.

Individual polymers (Table 1; all from (Sigma-Aldrich; St. Louis, unless indicated otherwise) were screened initially.

TABLE 1

| | Polymers Screened |
| --- | --- |
| A | Poly(1,4-butylene adipate) |
| B | Poly(ethylene adipate) |
| C | Poly(1,3-propylene succinate) |
| D | Poly(1,3-propylene glutarate) |
| E | Poly(1,3-propylene adipate) |
| F | Poly(D,L-lactide-co-caprolactone) lactide:caprolactone 40:60 |
| G | Poly(D,L-lactide-co-caprolactone) lactide:caprolactone 84:16 |
| H | Poly(1,4-butylene adipate), diol end-capped |
| I | Poly(ethylene adipate), dihydroxy terminated |
| J | Poly(lactide-co-glycolide) lactide:glycolide 50:50, MW_60,000 |
| K | Poly(lactide-co-glycolide) lactide:glycolide 50:50, MW_18,000, acid terminated |
| L | Poly(lactide) D:L 50:50 MW_25,000 |

TABLE 1-continued

Polymers Screened

| | |
|---|---|
| M | Poly(lactide-co-glycolide) lactide:glycolide 50:50, MW_65,000 |
| N | Poly(lactide-co-glycolide) lactide:glycolide 85:15, MW_60,000 |
| O | Poly(lactide-co-glycolide) lactide:glycolide 65:35, MW_58,000 |
| P | Poly(lactide-co-glycolide) lactide:glycolide 75:25, MW_100,000 |
| Q | Poly(lactide-co-glycolide) 1-lactide, lactide:glycolide 70:30, MW_22,000 |
| R | Poly(lactide-co-glycolide) lactide:glycolide 50:50, MW_100,000 |
| S | Poly(lactide) L:DL 60:40, MW_120,000 |
| T | Poly(lactide) D:L 50:50, MW_8,000, acid terminated |
| U | Poly(lactide-co-glycolide-co-glycol) lactide:glycolide:glycol 53:21:26 MW_80,000 |
| V | Poly(ethlyene glycol) MW_300 |
| W | Poly(lactide-co-glycolide) lactide:glycolide: 65:35 MW_14,000 |
| X | Poly(azelaic anhydride) |
| Y | Hyaluronan (Glycosan BioSystems) |
| Z | Alginate (Invitrogen) |
| a | Acrylamide |
| b | Gelatin |
| c | Methylcellulose |
| d | Agar |
| e | Control (Matrigel) |

Each single polymer spot contained soluble form of basement membrane purified from Engelbreth-Holm-Swarm (EHS) tumor containing laminin I, collagen IV, entactin; heparin sulfate proteoglycan (EHS basement membrane; 50 μg/ml). Hyaluronan hydrogel had the highest score from this screen, therefore, all other factor screens were performed using hyaluronan as the hydrogel. The results of the polymer screening are shown in FIG. 1. Values are averaged from experiments with both hESC and HDF cells.

Extracellular Matrix Factor Screening.

Individual extracellular matrix (ECM) factors (Table 2; all from Sigma-Aldrich; St. Louis, unless indicated otherwise) were screened as described above for polymers.

TABLE 2

Extracellular Matrix Factors Tested

| | |
|---|---|
| A | Laminin (5 μg/ml) |
| B | Fibronectin (5 μg/ml) |
| C | Vitronectin (6 μg/ml) |
| D | Collagen (10 μg/ml) |
| E | RGD peptide (40 μg/ml) |
| F | IKVAV peptide (50 μg/ml) |
| G | Soluble form of basement membrane purified from Engelbreth-Holm-Swarm (EHS) tumor (containing laminin I, collagen IV, entactin, heparin sulfate proteoglycan; 50 ug/ml) (EHS basement membrane) |
| H | Control (Matrigel) |

Figure 2:
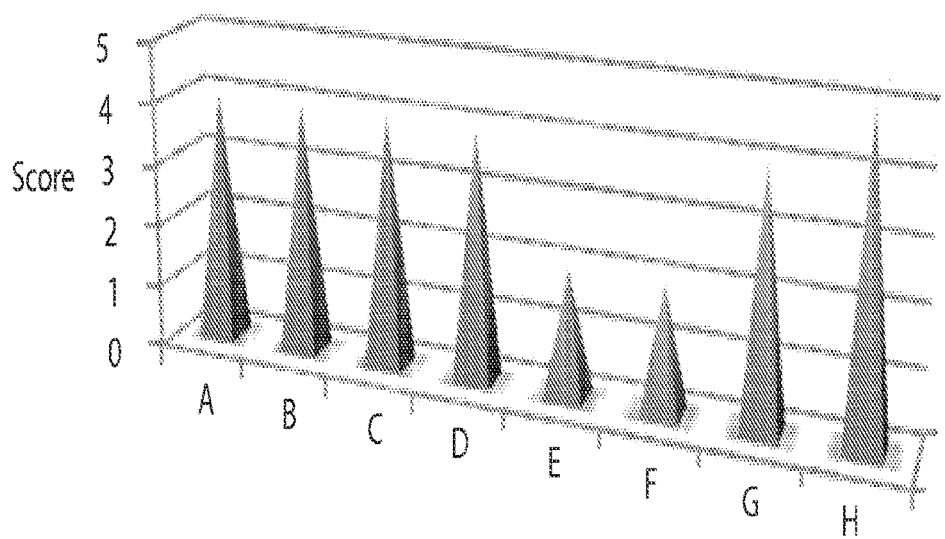
FIG. 2 is a plot of the scores of cell growth, survival and overall culture health in the presence of the various extracellular matrix factors listed in Table 2.

The results of the polymer screening are shown in FIG. 2. Based on this screening, laminin, fibronectin, vitronectin and EHS soluble form of basement membrane were selected for further study.

Individual Growth Factor Screening.

Individual growth factors (Table 3) were screened as described above for polymers.

TABLE 3

Growth Factors Tested

| | |
|---|---|
| A | Epidermal Growth Factor (EGF; 40 ng/ml) |
| B | Fibroblast Growth Factor, (FGF; 220 ng/ml) |
| C | Noggin (150 ng/ml) |
| D | BDNF |
| E | NGF |

TABLE 3-continued

Growth Factors Tested

| | |
|---|---|
| F | Insulin |
| G | IGF-1 |
| H | IGF-2 |
| I | PDGF |
| J | Control (Matrigel) |

Figure 3:
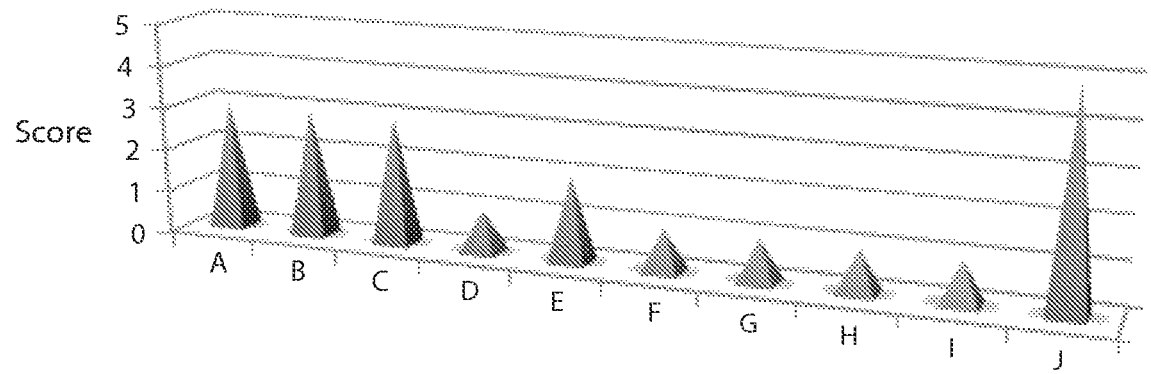
FIG. 3 is a plot of the scores of cell growth, survival and overall culture health in the presence of the growth factors listed in Table 3.

The results of the growth factor screening are shown in FIG. 3. Based on this screening, EGF, FGF and Noggin were selected for further study.

Crude Growth Factor Extract Screening.

Crude growth factors (Table 4) were screened as described above for polymers.

TABLE 4

Crude Factor Extracts Tested

| | |
|---|---|
| A | Fresh liver extract (50 μl/ml) |
| B | Liver Extract S100<br>Fresh liver extract S100 fraction<br>(Supernatant of extract centrifuged at 100,000 × g for 30 minutes) (50 μl/ml) |
| C | SIS<br>Pig Small Intestine Submucosa extract (50 μl/ml). |
| D | SIS-S100<br>Pig Small Intestine Submucosa (SIS) extract, S100 fraction (Supernatant of extract centrifuged at 100,000 × g for 30 minutes) (50 μl/ml). |
| E | Soluble EHS |
| F | Control (Matrigel) |

Figure 4:
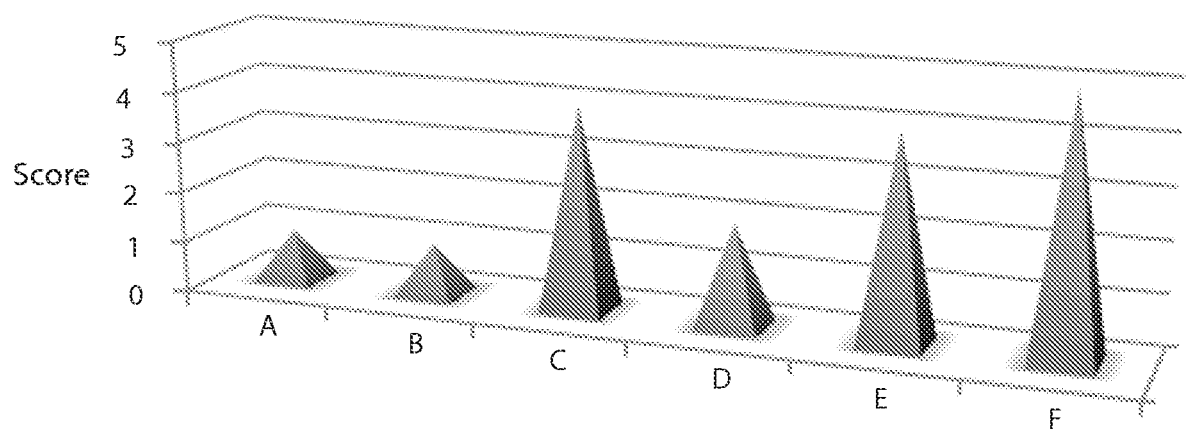
FIG. 4 is a plot of the scores of cell growth, survival and overall culture health in the presence of the crude factor extracts listed in Table 4.

The results of the crude growth factor extract screening are shown in FIG. 4. Based on this screening, SIS and Soluble EHS were selected for further study.

Example 2. Combinatorial Subtractive Optimization of Microenvironment Niche Composition To optimize the microenvironment niche for maintaining hES and HDF cells, a complete medium containing ECM factors, individual growth factors and crude growth factors as in EXAMPLE 1 that gave a score 3 or higher were combined to arrive at a Complete Media formulation: laminin (5 μg/ml), fibronectin (5 μg/ml), vitronectin (6 μm/ml); EGF; 40 ng/ml); FGF (220 ng/ml); Noggin (150 ng/ml) SIS (500 ml); and EHS (50 μm/ml) in mTeSR-1. To confirm the benefit of each component of the Complete Media, each factor a combinatorial subtractive screening was performed. Briefly, cells were grown on hyaluronan hydrogel polymer as described above in EXAMPLE 1 in either 2D (cells on the surface of polymerized hydrogel) or 3D (cells are embedded in the hydrogel) in Complete Media or Complete Media missing one of the components, as indicated below in Table 5.

TABLE 5

Components for Combinatorial Subtractive Screening

| | |
|---|---|
| A | Complete Media |
| B | Complete minus SIS |
| C | Complete minus Growth Factors |
| D | Complete minus ECM |
| E | Complete minus laminin |
| F | Complete minus fibronectin |
| G | Complete minus vitronectin |
| H | Complete minus EGF |
| I | Complete minus FGF |

TABLE 5-continued

| Components for Combinatorial Subtractive Screening | |
|---|---|
| J | Complete minus Noggin |
| K | Complete minus EHS |
| L | Control (Matrigel) |

Figure 5:
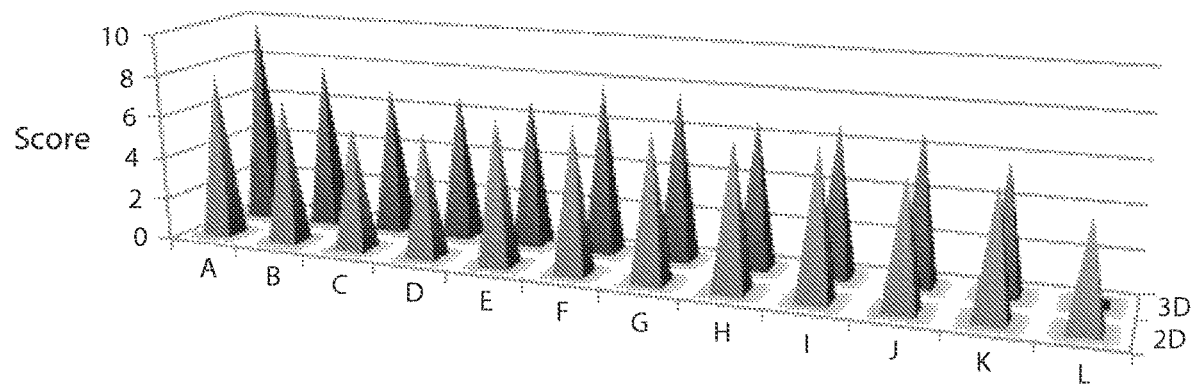
FIG. 5 is a plot of the scores of cell growth, survival and overall culture health for the combinatorial subtractive screening conditions listed in Table 5.

The results of the combinatorial subtractive screening are shown in FIG. 5. The results of this screening confirmed that the optimal growth results were obtained when cells were grown in the ES cell microenvironment niche provided by 3D culture with Complete Media. It should be noted that each of the combinations were tested in both 2D and 3D format and the 3D format yielded consistently higher scores.

Example 3: Chemical Induction of Pluripotency

ViPS strategies have focused on induction of pluripotency in somatic cells by introducing exogenous polynucleotides into the somatic cell via viral expression vectors. The polynucleotide express a discrete set of factors ("pluripotency factors") believed responsible for inducing pluripotency. We reasoned that compounds known to stimulate expression of these pluripotency factors could be substituted for the exogenous polynucleotides.

Reported studies indicated that one set of pluripotency factors that was sufficient for induction of pluripotency was OCT4, Sox2, Nanog, and Klf4. To test the possibility of chemical induction of pluripotency in human dermal fibroblasts, well known compounds affecting these pluripotency factors were substituted for expression of the pluripotency factors from viral expression vectors. Candidate compounds included those that affect the Wnt pathway because activation of this pathway had been reported to be involved in OCT 3/4, Sox-2, and Nanog activation. The initial compounds tested included: BIO (6-bromoindirubin-3'-oxime), a specific pharmacological inhibitor of glycogen synthase kinase known to stimulate Wnt signaling and maintain pluripotency in human and mouse embryonic stem cells (Sato et al., Nat. Med. (2004) 10:55-63); prostaglandin E2 (PGE2), reported to be an activator of Wnt pathway via "cross talk" at the beta-catenin signal level; valproic acid, a histone deacetylase (HDAC) inhibitor, and Wnt pathway activator (Bug et al. (2005) Cancer Res 65:2537-41). Valproic acid's influence on HDACs was also suggested to part in eliminating the need for KLF4 gene activation (Evans et al. (2007) J. of Biol. Chem. 282:33994-34028); and prostaglandin J2 (PGJ2), known to increase endogenous KLF4 gene expression levels (Chen & Tseng (2005) Mol. Pharmacol. 68:1203-13). These compounds were chosen for further experimentation since their mechanism of activity was previously determined and they appeared to activate the pluripotency signal transduction pathway (e.g. Wnt pathway).

Figure 6:
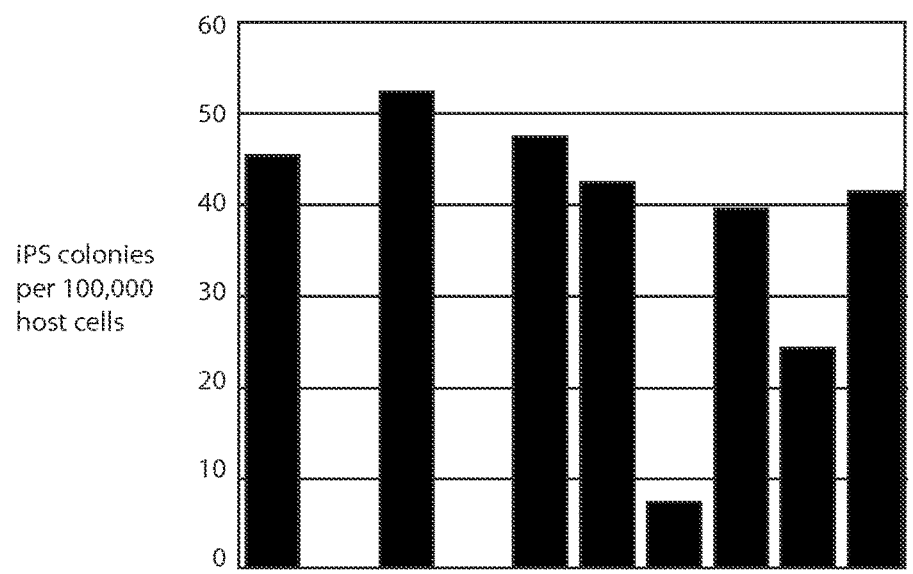
FIG. 6 shows the results of a preliminary ViPS pluripotency factor replacement experiment described in EXAMPLE 3. OCT4, Sox2, Nanog, and KLF4 refer to exogenous genes introduced into HDF cells using lentiviruses. BIO, PGE2, VA, and PGD2 refer chemical inducers (6-bromoindirubin-3'-oxime, prostaglandin E2, valproic acid, and prostaglandin J2, respectively that were used to replace one, two, three or all ViPS pluripotency factors.

Compounds were added to HDF cells grown in 3D ES cell microenvironment niche cultures (prepared as described above in EXAMPLES 1 and 2), to evaluate whether they would rescue iPS phenotype in the absence of individual pluripotency factors introduced retrovirally. ViPS cells, induced with lentiviral transduction of pluripotency factor genes (OCT4, Sox2, Nanog, Klf4) as described by Takahashi et al. ((2007), Cell 131:1-12). Data is presented as the number of colonies with iPS morphology observed per 100,000 host cells. The results summarized in FIG. 6 provide preliminary evidence in support of the hypothesis that compounds including BIO, PGE2, valproic acid and PGJ2, could be used to replace virally transduced pluripotency factors in induction of pluripotent status in somatic cells. Surprisingly, a cocktail of these four compounds only resulted in the rescue of the phenotype of ViPS cells using small molecules only.

Stem cell self renewal optimized 3-D hydrogel ES microenvironment niche conditions (as described in EXAMPLEs 1 and 2) were found necessary for chemical induction of iPS state. Pluripotency was not observed when standard tissue culture plates or those coated with Matrigel or methylcellulose were substituted for the 3D microenvironment conditions.

Example 4: Screening for Compounds Capable of Reprogramming of HDF Cells

To screen for additional and/or more effective compounds capable of reprogramming somatic cells to pluripotency, various compounds were tested for their effect on somatic HDF cells in optimized 3D microenvironment niche culture. For the initial screen, the ability of test compounds to affect genes known to be expressed in pluripotent cells was measured. HDF cells and biomaterial microarrays were prepared as follows.

Induction and Screening.

Replicate microspots were prepared in Complete Media and transfected with reporter constructs for genes critically expressed in pluripotent cells. The reporter constructs contained promoter regions of one of the genes listed in Table 6 operably linked to a green fluorescent protein (GFP) coding region in pGlow TOPO TA (Invitrogen).

TABLE 6

| Promoters for Pluripotency Gene Expression Reporter Constructs | | |
|---|---|---|
| Gene | Description | GenBank Identifier |
| OCT3/4 | POU class 5 homeobox 1 (POU5F1) | GI:11602730 |
| SOX2 | sex determining region Y box2 | GI:215820640 |
| LIN28 | lin28 homolog | GI:224589800 |
| KLF4 | Kruppel like factor 4 (gut) | GI:224589821 |

Briefly, a transient transfection mixture containing Lipofectamine 2000 (0.4 µl/24 µl total hyaluronan volume, Invitrogen) and promoter-Green Fluorescent Protein (GFP) construct in (500 ng) was added to each microspot.

Compound Libraries.

An in-house library of compounds (3600 compounds) was assembled by combining commercially available compound libraries and previously known activators of self renewal/stemness as well as potential self-renewal modulators of unknown mechanism of action. The libraries included compounds from: MicroSource library, which contained 2000 biologically active and structurally diverse compounds from known drugs, experimental bioactives, and pure natural products; including a collection of 720 natural products and their derivatives, a range of simple and complex oxygen-containing heterocycles, alkaloids, sesquiterpenes, diterpenes, pentacyclic triterpenes, sterols, and many other diverse representatives; and the Prestwick Chemical Library (see the world wide web at prestwickchemical "dot" fr), a collection of 880 high-purity chemical compounds selected for structural diversity and representing drug classes with a broad spectrum of therapeutic uses. More than 85% of its compounds are marketed drugs. Notably, the libraries included 6-bromoindirubin-3'-oxime (BIO), valproic acid, prostaglandin E2 (PGE2), and prostaglandin J2 (PGJ2).

Many compounds in the library could be assigned to one of 14 high interest categories based on known targets and pathways affected, and reported outcomes, as shown in Table 7.

TABLE 7

Categories of Compounds Screened

| Compound Category | Target | Pathway | Outcome (Promotes) |
|---|---|---|---|
| 1 | GSK-3 | Wnt | Self Renewal |
| 2 | GSK-3 | Wnt | Differentiation |
| 3 | TBD | Wnt | Self Renewal |
| 4 | TBD | Wnt | Differentiation |
| 5 | Smoothened | Hedgehog | Anti-Proliferation |
| 6 | TBD | Hedgehog | Anti-Proliferation |
| 7 | TBD | Hedgehog | Differentiation |
| 8 | TBD | NF-kB | Self Renewal |
| 9 | TBD | NF-kB | Differentiation |
| 10 | Cox-1 | PGE-2 | Anti-Proliferation |
| 11 | Cox-1 | PGE-2 | Anti-Proliferation |
| 12 | PKC | PKC | Apoptosis, Necrosis |
| 13 | TBD | TBD | Self Renewal |
| 14 | TBD | TBD | Differentiation |

Library screening was performed by including dilution series of each compound in mTeSR-1 medium, to HDF cells embedded in 3D hyaluronan hydrogel microenvironment niche culture optimized as described above in EXAMPLES 1 and 2.

Figure 7:
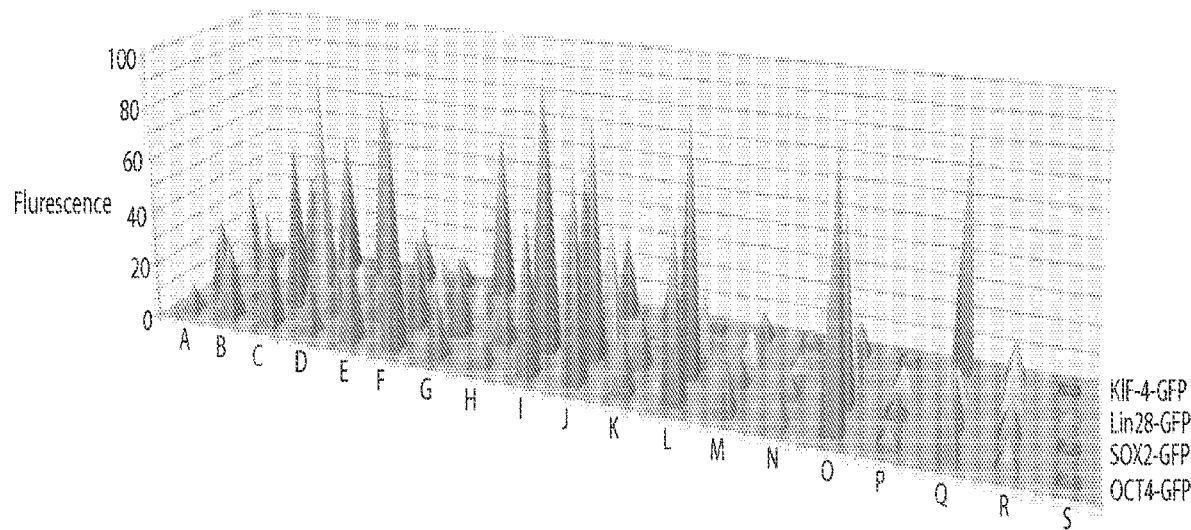
FIG. 7 shows the results of a screen of compounds for activation of the reporter constructs listed in Table 6 in HDF cells in a pluripotent stem cell microenvironment niche culture of the invention. Units shown represent relative fluorescence units from a green fluorescent protein reporter. Compounds tested are listed in Table 8.

After 4 days of incubation with target compounds, relative fluorescence from expression of the GFP constructs was recorded using a fluorescent microplate reader. Values were normalized to reflect percent fluorescence of control (ViPS) cells. A sampling data of this high-throughput screen using the compounds listed in Table 8 is shown in FIG. 7.

TABLE 8

Exemplary Compounds Screened

| A | D1-234 |
|---|---|
| B | D7-874 |
| C | D2-435 |
| D | D7-988 |
| E | D2-2334 |
| F | D9-6452 |
| G | D16-34675 |
| H | D3-8976 |
| I | D12-2234 |
| J | D2-6542 |
| K | D6-982 |
| L | D21-8765 |
| M | D23-1276 |
| N | D6-987 |
| O | D10-8976 |
| P | D-2217 |
| Q | D9-9811 |
| R | D14-3245 |
| S | D9-7765 |

Compounds that activated expression of one or more of the target promoters were scored as positive. A set of positive compounds from the screen shown in FIG. 6 were: D9-6452: 6-bromoindirubin-3'-oxime (BIO); D10-8976: Valproic Acid; D3-8976: Indirubin-5-nitro-3'-oxime (INO); D21-8765: 2-(3-(6-Methylpyridin-2-yl)-1H-pyrazol-4-yl)-1,5-naphthyridine; D12-2234: 1-(4-Methylphenyl)-2-(4,5,6,7-tetrahydro-2-imino-3(2H)-benzothiazolyl)ethanone HBr, (Pifithrin-alpha); D9-9811: Prostaglandin J2; D2-6542: Prostaglandin E2.

Positive compound hits were selected, rescreened in triplicate and the best candidates chosen on the basis of highest level of promoter activation for one or more target promoters tested. Through multiple rounds of repeat experimentations with a broad range of compound concentrations, optimum concentration for each of the selected compounds was empirically determined. The optimized concentrations of seven compounds are summarized in Table 9.

TABLE 9

Optimized Chemical Induction Component Concentrations

| Chemical Induction Component | Optimized Concentration |
|---|---|
| 6-bromoindirubin-3'-oxime (BIO) | 4 μM |
| Indirubin-5-nitro-3'-oxime (INO) | 4 μM |
| Valproic Acid | 2 mM |
| D21-8765: 2-(3-(6-Methylpyridin-2-yl)-1H-pyrazol-4-yl)-1,5-naphthyridine | 25 mM |
| 1-(4-Methylphenyl)-2-(4,5,6,7-tetrahydro-2-imino-3(2H)-benzothiazolyl)ethanone HBr, Pifithrin-alpha | 30 μM |
| Prostaglandin J2 | 10 μM |
| Prostaglandin E2 | 10 μM |

Example 6: Optimization of Chemical Induction of Pluripotency

Figure 8:
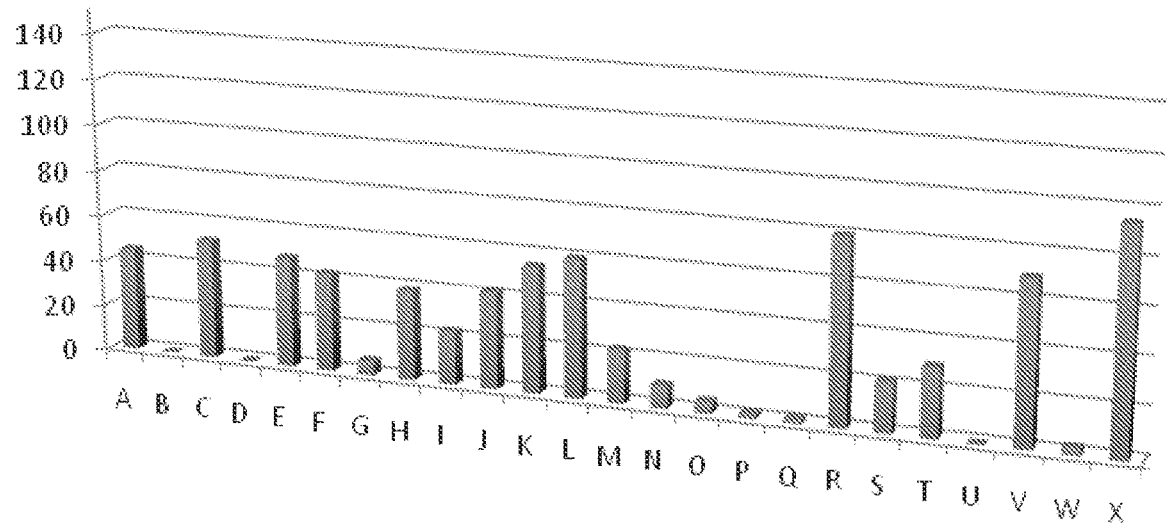
FIG. 8 shows the results of promoter-GFP expression in cells treated with combinations of virally introduced pluripotency factors and chemical inducers of pluripotency as described in EXAMPLE 6.

FIG. 8 shows a sampling of data generated using compounds that increased expression of promoters from pluripotency genes in the promoter reporter assay screen as described in EXAMPLE 5. Probable candidates were chosen based on their level of influence on one or more promoters. Also positive hits that had a known mechanism of activity on related signal transduction pathways were favored. Each compound cocktail was included in a long term induction protocol of CiPSC from HDF. In all cases a serial concentration range of each member of each compound cocktail were examined to empirically determine optimal compound/cocktail concentrations. These optimum concentrations were then used in comparative experiments, result of which are shown in this figure. Number of CiPSC colonies generated per 100000 starting number of HDF cells (Y-axis) was the experiment's end point analysis.

Control experiments were ViPS derivation with lentiviral vectors to induce pluripotency (A-J). K-W show attempts to use small molecule inducer cocktails to rescue the iPS phenotype in the absence of genetic induction. Most successful cocktail is that shown in R. This cocktail was used for further validation studies. In further experimental optimization studies it was determined that synchronization of cells increased efficiency of induction. For example treatment with Colcemid, resulted in increased efficiency (see FIG. 7, X)

Members of this cocktail are:
D9-6452: 6-bromoindirubin-3'-oxime (BIO). Previously known mechanism: Wnt pathway activation.
D10-8976: Indirubin-5-nitro-3'-oxime (INO). Previously known mechanism: Wnt pathway activation.
D3-8976: Valproic Acid. Previously known mechanism: HDAC inhibitor, Wnt pathway activator, increases KLF4 expression.
D21-8765: 2-(3-(6-Methylpyridin-2-yl)-1H-pyrazol-4-yl)-1,5-naphthyridine. Previously known mechanism: inhibitor of TGFbeta pathway.
D12-2234: 1-(4-Methylphenyl)-2-(4,5,6,7-tetrahydro-2-imino-3(2H)-benzothiazolyl)ethanone HBr, Pifithrin-alpha. Previously known mechanism: p53 inhibition.

D9-9811: Prostaglandin J2. Previously known mechanism: Increase endogenous KLF4 levels.

D2-6542: Prostaglandin E2. Wnt pathway activator, "crosstalk" at the Beta-Catenin signal level.

Based on these findings, we concluded that in order to activate the pluripotency pathway and induce reprogramming of somatic cells the following types of intercellular signal modulation are required by the CiPS small molecule cocktails:

1) Molecules that activate Wnt pathway and display characteristic pluripotency gene activation shown.
2) Molecules that activate Cyclooxygenase pathway and its cross talk with wnt pathway and display characteristic pluripotency gene activation shown.
3) Histone Deacetylases that activate the pluripotency pathway and display characteristic pluripotency gene activation shown.
4) Molecules that increase Sox-2 expression and display characteristic pluripotency gene activation shown.
5) Molecules that increase Nanog expression and display characteristic pluripotency gene expression.
6) Molecules that inhibit p53 and related pathways and display characteristic pluripotency gene activation shown.
7) Synchronization of cells prior to or during induction of CiPSC improves efficiency.

Example 7: Induction of Pluripotency in Human Dermal Fibroblasts

Preparation of 3D Format Cultures.

HA and CL were prepared under sterile conditions according manufacturer's directions. HDF were prepared. 8.0 mL of HA was mixed with 8.0 mL of TMC. The following additives were added to the mixture in a total volume of ≤4 mL to the indicated final concentrations: laminin (5 µg/ml); fibronectin (5 µg/ml); vitronectin (6 µg/ml); Epidermal Growth Factor (40 ng/ml); Fibroblast Growth Factor (220 ng/ml); Noggin (150 ng/ml); Pig Small Intestine Submucosa (SIS) extract, (50 µl/ml); soluble form of basement membrane purified from Engelbreth-Holm-Swarm (EHS) tumor containing laminin I, collagen IV, entactin, heparin sulfate proteoglycan. (50 µg/ml). The mixture was then inverted and vortexed for 10 minutes at 2° C. This final solution was referred to as complete HAF (HAFC).

Human dermal fibroblasts (HDF) 0.2 mL cells, were added to 2 mL HAFC and the mixture gently pipeted to mix. CL (0.5 mL) of was then added to the cell mixture to form hydrogels, giving a final cell density of 50 cells/ml and 1 ml was dispensed per well of a 24 culture plates. The plates were then incubated at 37° C. incubator with 5% CO2 for 1 hour to allow HAFC to gel. After gelling, 1.8 mL of mTeSR-1 culture media was added to each well, and the cells incubated at 37° C. incubator with 5% CO2 with a change of mTeSR-1 media every two days. During the first week, the media included 0.01 µg/ml of colcemid.

Induction.

Induction was initiated 1 week after culture and continued for three weeks. The following Inducer Drug Cocktail (IDC) was included in mTeSR medium: 6-bromoindirubin-3'-oxime (4 µM); indirubin-5-nitro-3'-oxime (4 µM); valproic acid (2 mM); 2-(3-(6-methylpyridin-2-yl)-1H-pyrazol-4-yl)-1,5-naphthyridine (25 mM), 1-(4-methylphenyl)-2-(4,5,6,7-tetrahydro-2-imino-3(2H)-benzothiazolyl)ethanone HBr, pifithrin-alpha (30 µM); prostaglandin J2 (10 µM), and prostaglandin E2 (10 µM). Cell culture was continued for a total of 32 days after initial plating.

Cells were recovered by adding using 500 µL collagenase/hyaluronidase solution (diluted 1:2 in mTeSR-1 media) per 100 µL of hydrogel with gentle shaking overnight at 37° C. The cells were recovered by centrifugation at 1500 rpm for five minutes and washed with PBS. Recovered cells were resuspended in 0.5 mL of mTeSR media without chemical inducers.

CiPS cells were subcloned and propagated on the surface of HAFC (2-D Culture) according to standard tissue culture protocols.

Example 8: Validation of Cell Reprogramming

Pluripotency Gene Expression.

RT-PCR was performed to measure expression of pluripotency associated genes. Briefly, total cellular RNA was extracted from $5 \times 10^6$ CiPS cells using a RNeasy Protect Mini kit (Qiagen; Valencia, Calif.), according to the manufacturer's instructions, and reverse transcribed using a SuperScript III First-Strand Synthesis System RT-PCR (Invitrogen). The cDNA was amplified by PCR using Accuprime Taq DNA polymerase system (Invitrogen).

Primers used for analysis of endogenous CiPS gene expression are shown in Table 10.

TABLE 10

Primers for Gene Expression Analysis

| Gene | Primer Name | Primer Sequence | SEQ ID NO |
|---|---|---|---|
| hNANOG | hNANOG-F | 5'-GCAGAAGGCCTCAGCACCTA-3' | SEQ ID NO: 1 |
|  | hNANOG-R | 5'-AGGTTCCCAGTCGGGTTCA-3' | SEQ ID NO: 2 |
| hOCT4 | hOCT4-F | 5'-GCTCGAGAAGGATGTGGTCC-3' | SEQ ID NO: 3 |
|  | hOCT4-R | 5'-CGTTGTGCATAGTCGCTGCT-3' | SEQ ID NO: 4 |
| hSOX2 | hSOX2-F | 5'-CACTGCCCCTCTCACACATG-3' | SEQ ID NO: 5 |
|  | hSOX2-R | 5'-TCCCATTTCCCTCGTTTTCT-3' | SEQ ID NO: 6 |
| hKLF4 | hKLF4-F | 5'-GCGAACTCACACAGGCGAGAAACC-3' | SEQ ID NO: 7 |
|  | hKLF4-R | 5'-TCGCTTCCTCTTCCTCCGACACA-3' | SEQ ID NO: 8 |
| hREX-1 | hREX-1-F | 5'-GGCTTCCCTGACAGATACC-3' | SEQ ID NO: 9 |
|  | hREX-1-R | 5' CCTTCGAACGTGCACTGATA 3' | SEQ ID NO: 10 |
| hGAPDH-R | hGAPDG-F | 5' ACCACAGTCCATGCCATCAC 3' | SEQ ID NO: 15 |
|  | hGAPDH-R | 5' TCCACCACCCTGTTGCTGTA 3 | SEQ ID NO: 16 |

Figures 9, 10:
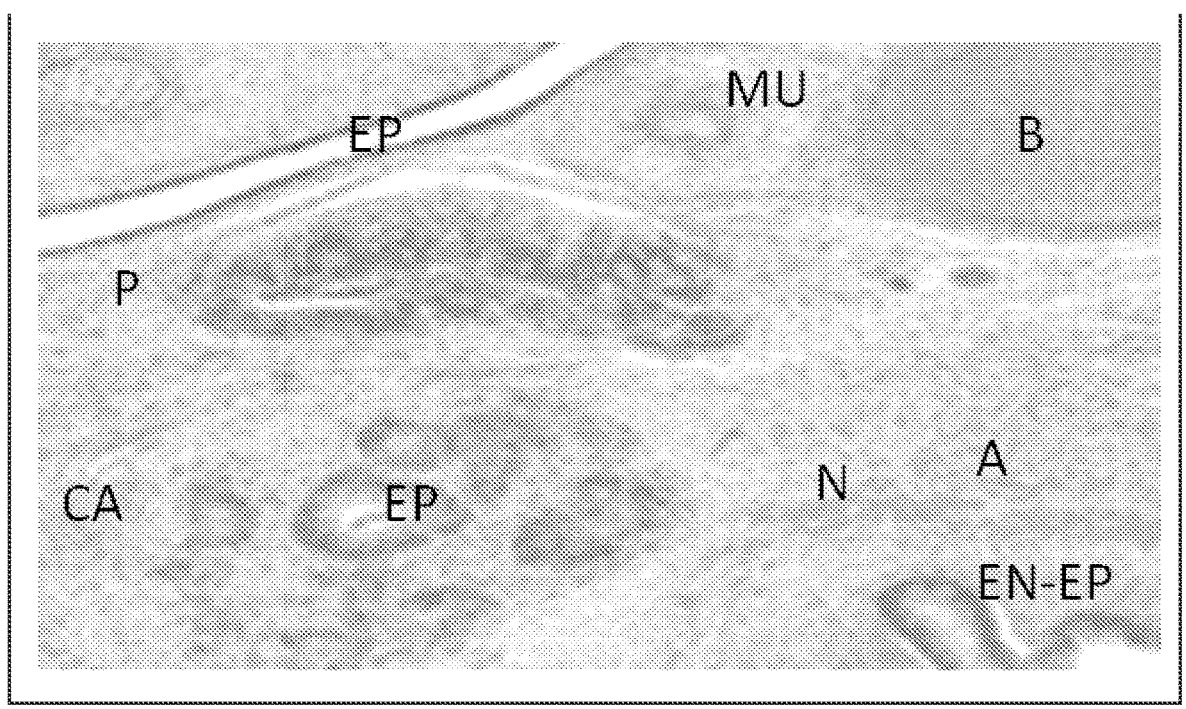
FIG. 9 shows the results of RT-PCR of CiPS cells using constructs containing the primers listed in Table 10.
FIG. 10 is a section of a teratoma generated from CiPS cells as described in EXAMPLE 8.

PCR products were separated by electrophoresis on a 2% agarose gel, stained with ethidium bromide and visualized by UV illumination. The results of this analysis are shown in FIG. 9.

Pluripotency Biomarker Expression.

Cells were fixed in 4% paraformaldehyde in PBS and immunostained according to standard protocols using the following primary antibodies: SSEA4 (mouse monoclonal, Developmental Studies Hybridoma Bank); Tra 1-60, (mouse monoclonal, Chemicon International); hSOX2 (goat polyclonal, R&D Systems); Oct-3/4 (mouse monoclonal, Santa Cruz Biotechnology); hNANOG (goat polyclonal R&D Systems); appropriate Molecular Probes Alexa Fluor® dye conjugated secondary antibodies (Invitrogen) were used. The results of this analysis are summarized in Table 11.

TABLE 11

Biomarker Expression of hES Cells and CiP Cells

| Marker | hESC | CiPC |
|---|---|---|
| SSEA-1 | — | — |
| SSEA-3 | + | + |
| SSEA-4 | + | + |
| TRA-1-60 | + | + |
| TRA-1-81 | + | + |
| OCT4 | + | + |

Mouse Teratoma Analysis.

Approximately 1-3×10$^6$ CiPSC were injected subcutaneously into the testes of nude mice SCID mice (Jackson labs) anesthetized with isoflurane. Five to 6 weeks after injection, teratomas formed and were dissected, fixed overnight in 10% buffered formalin phosphate and embedded in paraffin. Sections were stained with haematoxylin and eosin for further analysis. Tissue sections were analyzed by light microscopy as shown in FIG. 10. Regions representing the following tissues were observed and marked proving presence of tissues from all three main somatic germ layers (Ectoderm, Mesoderm, Endoderm). P: Pigmented Epithelium, EP: Ectodermal Epithelium, B: Bone (Mesoderm), CA: Cartilage (Mesoderm), EN-EP: Endodermal Epithelium, MU: Striated Muscle (Mesoderm), A: Adipose Tissue, N: Neural Tissue (Ectoderm).

Methylation Analysis

Figure 11:
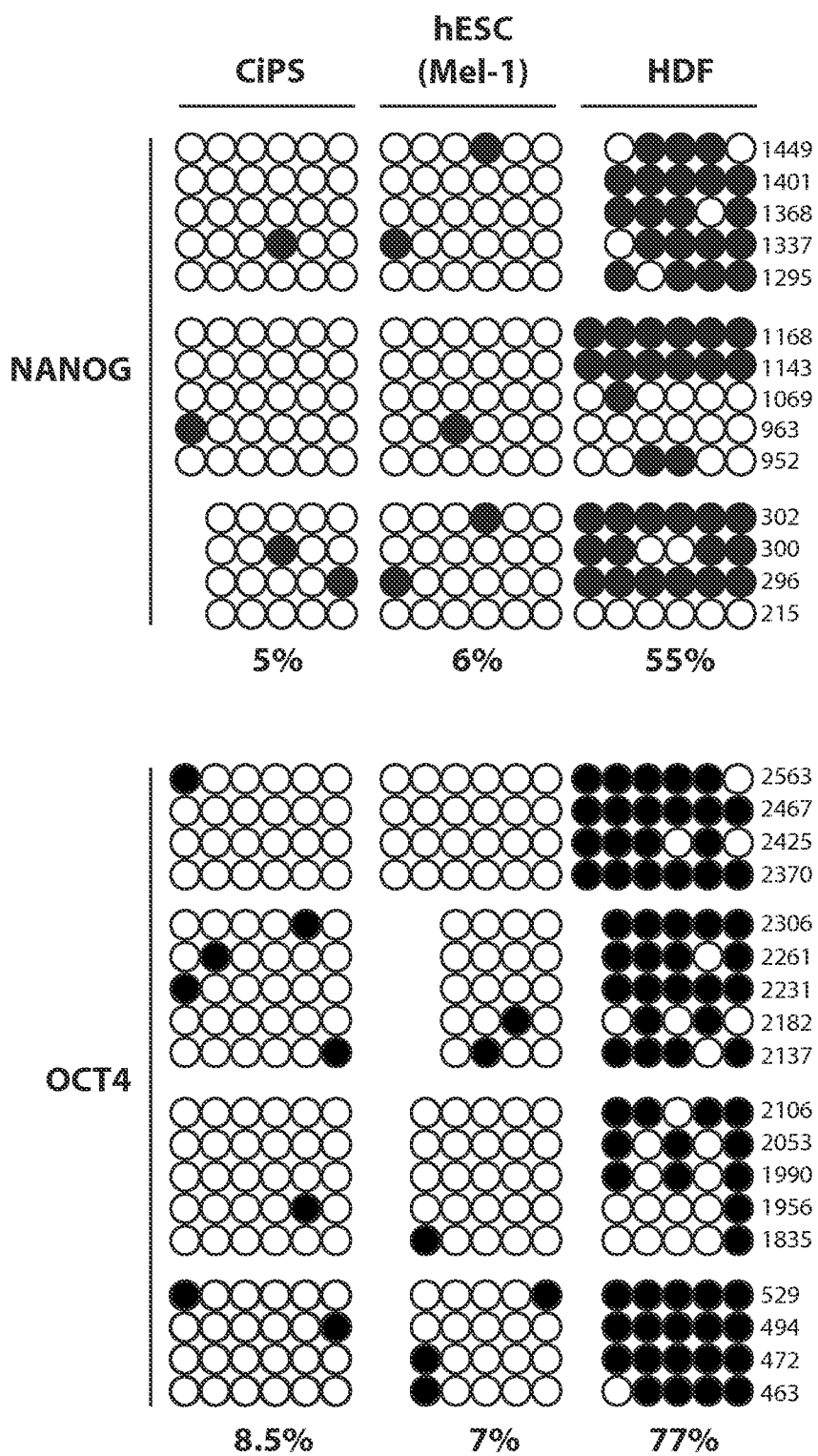
FIG. 11 is representation of the methylation status of CpGs in the promoter of the Nanog and OCT4 genes from CiPS cells, hES cells and HDF cells as described in EXAMPLE 8.

DNA was isolated from CiPSC and hESC and treated with bisulfite using the EpiTect Bisulfite Kit (Qiagen) according to manufacturer's instructions. Amplified products were purified using gel filtration columns (Qiagen), cloned into the pCR2.1-TOPO vector (Invitrogen), and sequenced with M13 forward and reverse primers. Unmethylated or methylated CpGs were determined, as shown in FIG. 11. Open and closed circles indicate unmethylated and methylated CpG, respectively. Numbers (right) indicate CpG locations. Percentages of CpG methylation are shown. Percent methylation values for Oct 4 and Nanog promoter regions are similar between hESC and CiPSC.

What is claimed is:

1. A composition for reprogramming at least one somatic cell to a pluripotent stem cell, the composition comprising:
   a polymer hydrogel that further comprises a polyether cross linker; valproic acid; and
   at least one reprogramming agent, wherein the at least one reprogramming agent is a signal transduction pathway modulator.

2. The composition of claim 1, wherein the polyether cross linker is polyethylene glycol diacrylate.

3. A composition is for reprogramming at least one somatic cell to a pluripotent stem cell, the composition comprising:
   a polymer hydrogel;
   valproic acid; and
   at least one reprogramming agent, wherein the at least one reprogramming agent is thiol-modified hyaluronan.

4. A composition for reprogramming at least one somatic cell to a pluripotent stem cell, the composition comprising:
   a polymer hydrogel;
   valproic acid; and
   at least one reprogramming agent, wherein the at least one reprogramming agent is chosen from the group consisting of 6-bromoindirubin-3'-oxime (BIO); indirubin-5-nitro-3'-oxime (INO); 2-(3-(6-Methylpyridin-2-yl)-1H-pyrazol-4-yl)-1,5-napthyridine; 1-4(-Methylphenyl)-2-(4,5,6,7-tetrahydro-2-imino-3(2H)-benzothiazolyl) ethanone HBr (Pifithrin-α); prostaglandin J2; and prostaglandin E2.

5. A composition for reprogramming cells, the composition comprising:
   a polymer hydrogel;
   valproic acid; and
   at least one signal transduction pathway modulator chosen from the group consisting of Wnt, Hedgehog, cyclooxygenase, p53, NF-κB, PKC, PGE-2 and combinations thereof.

6. The composition of claim 5, wherein the composition is capable of reprogramming at least one somatic cell to pluripotency resulting in at least one pluripotent cell.

7. The composition of claim 6, wherein the at least one pluripotent cell is a somatic stem cell.

8. The composition of claim 5, further comprising at least one growth factor.

9. The composition of claim 8, wherein the at least one growth factor is selected from the group consisting of epidermal growth factor; fibroblast growth factor; Noggin; BDNF; NGF; Insulin; IGF-1; IGF-2; and PDGF.

10. The composition of claim 5, wherein at least one signal transduction pathway further comprises at least one component selected from the group consisting of 6-bromoindirubin-3'-oxime (BIO); indirubin-5-nitro-3'-oxime (INO); 2-(3-(6-Methylpyridin-2-yl)-1H-pyrazol-4-yl)-1,5-napthyridine; 1-4(-Methylphenyl)-2-(4,5,6,7-tetrahydro-2-imino-3(2H)-benzothiazolyl) ethanone HBr (Pifithrin-α); prostaglandin J2; and prostaglandin E2.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
gcagaaggcc tcagcaccta                                         20

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 2
aggttcccag tcgggttca                                          19

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 3
gctcgagaag gatgtgtcg                                          19

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 4
cgttgtgcat agtcgctgct					20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 5
cactgcccct ctcacacatg					20

<210> SEQ ID NO 6
<211> LENGTH: 21
<212> TYPE: DNA
<213> ORGANISM: Artificial Sequence
<220> FEATURE:
<223> OTHER INFORMATION: synthetic oligonucleotide primer

<400> SEQUENCE: 6
tcccatttcc ctcgtttttc t					21

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide primer

<400> SEQUENCE: 7
gcgaactcac acaggcgaga aacc				24

<210> SEQ ID NO 8
<211> LENGTH: 23
<212> TYPE: DNA
<213> ORGANISM: Artificial Sequence
<220> FEATURE:
<223> OTHER INFORMATION: synthetic oligonucleotide primer

<400> SEQUENCE: 8
tcgcttcctc ttcctccgac aca				23

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 9
ggcttccctg acagatacc					19

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 10
ccttcgaacg tgcactgata					20

<210> SEQ ID NO 11

```
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 11
accacagtcc atgccatcac                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 12
tccaccaccc tgttgctgta                                              20
```